US006972326B2

(12) United States Patent
Haugland et al.

(10) Patent No.: US 6,972,326 B2
(45) Date of Patent: Dec. 6, 2005

(54) LABELING OF IMMOBILIZED PROTEINS USING DIPYRROMETHENEBORON DIFLUORIDE DYES

(75) Inventors: Richard P. Haugland, Eugene, OR (US); Karen J. Martin, Eugene, OR (US); Wayne F. Patton, Eugene, OR (US)

(73) Assignee: Molecular Probes, Inc., Eugene, OR (US)

( * ) Notice: Subject to any disclaimer, the term of this patent is extended or adjusted under 35 U.S.C. 154(b) by 361 days.

(21) Appl. No.: 10/005,050

(22) Filed: Dec. 3, 2001

(65) Prior Publication Data

US 2005/0186641 A1    Aug. 25, 2005

(51) Int. Cl.$^7$ .................. C07K 17/06; G01N 21/76; G01N 33/533
(52) U.S. Cl. .................. 530/409; 435/7.5; 435/7.9; 436/86; 436/172; 436/546
(58) Field of Search .................. 530/409; 436/546, 436/86, 172; 435/7.5, 7.9

(56) References Cited

U.S. PATENT DOCUMENTS

| | | |
|---|---|---|
| 4,774,339 A | 9/1988 | Haugland et al. |
| 4,810,636 A | 3/1989 | Corey |
| 4,931,223 A | 6/1990 | Bronstein et al. |
| 4,962,192 A | 10/1990 | Schaap |
| 5,187,288 A | 2/1993 | Kang et al. |
| 5,196,306 A | 3/1993 | Bobrow et al. |
| 5,248,782 A | 9/1993 | Haugland et al. |
| 5,270,163 A | 12/1993 | Gold et al. |
| 5,274,113 A | 12/1993 | Kang et al. |
| 5,316,906 A | 5/1994 | Haugland et al. |
| 5,338,854 A | 8/1994 | Kang et al. |
| 5,433,896 A | 7/1995 | Kang et al. |
| 5,443,986 A | 8/1995 | Haughland et al. |
| 5,451,663 A | 9/1995 | Kang et al. |
| 5,583,001 A | 12/1996 | Bobrow et al. |
| 5,719,031 A | 2/1998 | Haugland et al. |
| 5,731,158 A | 3/1998 | Bobrow et al. |
| 6,127,134 A | 10/2000 | Minden et al. |
| 6,130,101 A | 10/2000 | Mao et al. |
| 6,162,931 A | 12/2000 | Gee et al. |

OTHER PUBLICATIONS

Gold, et al., Diversity of Oligonucleotide Functions, Ann. Rev. Biochem. 64, 763-97 (1995).
Osborne, et al., Nucleic Acid Selection and the Challenge of Combinatorial Chemistry, Chem. Rev. 97, 349-70 (1997).
Szewczyk, et al., Fluorescent Staining of Proteins Transferred to Nitrocellulose Allowing for Subsequent Probing with Antisera, Anal. Biochem. 164, 303-06 (1987).
Dunn, Electroblotting of Proteins from 2-D Polyacrylamide Gels, Meth. Mol. Biol. vol. 112, Ch.35, 313-18 (1999).
Berggren, et al., A Luminescent Ruthenium Complex for Ultrasensitive Detection of Proteins Immobilized on Membrane Supports, Anal. Biochem. 276, 129-43 (1999).
Pryor, et al., Immunodetection after Complete Destaining of Coomassie Blue-Stained Proteins on Immobilon-PVDF, Anal. Biochem. 202, 100-04 (1992).
Ducret, et al., A general method for the rapid characterization of tyrosine-phosphorylated proteins by mini two-dimensional gel electrophoresis, Electrophoresis 21, 2196-2208 (2000).
Schaerfke, et al., Method for the Immunological Detection of Silver-Stained Proteins on Nitrocellulose Membranes, BioTechniques 30, 266-72 (2001).
Patton, A thousand points of light: The application of fluorescence detection technologies to two-dimensional gel electrophoresis and proteomics, Electrophoresis 21, 1123-44 (2000).
Alba, et al., Rapid fluorescent monitoring of total protein patterns on sodium dodecyl sulfate-polyacrylamide gels and Western blots before immunodetection and sequencing, Electrophoresis 19, 2407-11 (1998).
Kemper, et al., An improved, luminescent europium-based for detection of electroblotted proteins on nitrocellulose or polyvinylidene difluoride membranes, Electrophoresis 22, 881-89 (2001).
Ganesh, et al., Rapid staining of proteins on polyacrylamide gels and nitrocellulose membranes uisng a mixture of fluorescent dyes, J. Biochem. Biophys. Methods 46, 31-38 (2000).
R. Haugland, Molecular Probes Handbook of Fluorescent Probes and Research Chemicals, 6$^{th}$ Edition., (1996) and its subsequent 7$^{th}$ Edition, and 8$^{th}$ Edition updates on CD-ROM in Nov. 1999 and May 2001.
R. Haugland, Molecular Probes Handbook of Fluorescent Probes and Research Chemicals, 6$^{th}$ Edition at p. 14 (1996).
Jones, et al, Quenched BODIPY Dye-Labeled Casein substrates for the Assay of Protease Activity by Direst Fluorescence Measurement, Anal. Biochem. 251, 144-52 (1997).
U.S. Appl. No. 09/970,215, to Haugland et al. (2001).
U.S. Appl. No. 09/969,853, to Leung et al. (2001).
Patton, Making Blind Robots See: The Synergy Between Fluorescent Dyes and Imaging Devices in Automated Proteomics, BioTechniques 28, 944-57 (2000).

*Primary Examiner*—Mary E. Ceperley
(74) *Attorney, Agent, or Firm*—Koren Anderson; Chris Buntel

(57) ABSTRACT

The invention describes methods for labeling or detecting of immobilized poly(amino acids), including peptides, polypeptides and proteins, on membranes and other solid supports, using fluorescent dipyrromethneboron difluoride dyes. Such immobilized poly(amino acids) are labeled or detected on blots or on arrays of poly(amino acids), or are attached to immobilized aptamers.

59 Claims, No Drawings

LABELING OF IMMOBILIZED PROTEINS USING DIPYRROMETHENEBORON DIFLUORIDE DYES

FIELD OF THE INVENTION

The invention relates to labeling or detecting of poly (amino acids), including peptides, polypeptides and proteins, that are immobilized on membranes and other solid supports, using dipyrrometheneboron difluoride dyes.

BACKGROUND OF THE INVENTION

Poly(amino acids) are typically immobilized on membranes and other solid supports, as in blots or arrays, to enable analysis of the poly(amino acids). Labeling or detection of such immobilized poly(amino acids) is of great importance in a multitude of diverse activities, ranging from basic research to enzyme production, forensics analysis and diagnostics. When analyzing the immobilized poly(amino acids), ideally the total poly(amino acid) profile is labeled in a way that will not interfere with other subsequent analytical methods that may be directed at specific targets within the profile.

When analyzing complex mixtures of proteins and other poly(amino acids), e.g., mixtures extracted from cells, cell organelles, tissues, or other biological samples, the first step involves some method of separating such complex mixtures into discrete locations or bands, typically by 1-D or 2-D gel electrophoresis. Proteins in a given band are often identified by using a specific binding pair member, such as an antibody or lectin, that binds selectively to the proteins in that band. However, in order to be accessible to antibodies or other specific binding pair members, the protein bands must first be transferred from the gel to a solid support (electroblotted), such as a membrane. In some cases, the complex mixtures are generated in the form of arrays that are already immobilized on a solid support, and the specific binding pair member is used to probe the array of immobilized proteins or other poly(amino acids) for those having certain defined characteristics. In addition to the more traditional arrays of proteins, the discovery of the SELEX® (Systematic Evolution of Ligands by EXponential enrichment) process enabled the identification of nucleic acid-based ligands, referred to as aptamers, that recognize molecules other than nucleic acids, including proteins, with high affinity and specificity (Ann. Rev. Biochem. 64, 763 (1995); Chem. Rev. 97, 349 (1997) and U.S. Pat. No. 5,270,163). In general, arrays of aptamers are bound to a solid support, and after a mixture of proteins or other poly(amino acids) is applied to the aptamer array, unbound poly(amino acids) are removed. The poly(amino acids) that are immobilized by binding to the aptamer array can be counterstained and probed.

In all cases, the specific binding pair members that are used to identify proteins in a band or location of interest can also be used to ascertain a number of important characteristics of the protein, including the presence and quantity of the protein in the band, the molecular weight of the protein, and the efficiency of protein extraction or separation. Such specific binding pair members, however, are only useful for the analysis of the proteins that are selectively bound by the specific binding pair member and do not yield any information about the proteins in other bands. Therefore, a counterstain is typically used to detect all the other proteins in the mixture to provide a frame of reference for the analysis.

Counterstains for proteins like Coomassie Brilliant Blue (CBB), Amido Black, silver nitrate (silver staining), and colloidal gold are often used as calorimetric counterstains for electroblotted proteins (Anal. Biochem. 164, 303 (1987)). Although most of these methods have been in common use for many years, they suffer from certain limitations. CBB staining is easy to perform and shows good reproducibility but is not very sensitive and only allows the detection of the major components within a protein sample (typically, not more than 200–300 spots on a blot from a cell extract that may actually contain thousands of individual proteins). In addition, the colorimetric counterstains such as Amido Black and CBB bind so tightly to proteins that destaining is difficult and residual counterstain often blocks epitopes for subsequent immunodetection (Meth. Mol. Biol. Ch. 35, 313 (1999); Anal. Biochem. 276, 129 (1999); Anal. Biochem. 202, 100 (1992)). Silver staining is up to 100× more sensitive than CBB staining, which makes it suitable for the detection of trace components within a protein sample (the detection limit is ~0.1 ng protein), and is still a method of choice for analytical gels. The major drawbacks to silver staining are the poor reproducibility, the limited dynamic range, and the fact that certain proteins stain poorly, negatively or not at all. Silver staining is also a procedure that is labor intensive and requires carefully timed steps to achieve reproducibility. Membranes stained with colloidal gold have also been found to generate heavy backgrounds after applying chemiluminescence-based immunodetection methods (Electrophoresis 21, 2196 (2000)), and staining lightly enough to yield useful results resulted in poor reproducibility as the endpoint had to be determined subjectively by the practitioner. Typically, all of these counterstaining procedures require that replicate blots be run, one stained with a colorimetric detection technique and the other blot probed for specific proteins using immunological methods. However, in order to identify proteins, the two blots have to be aligned. This leads to problems because often two blots from the same sample may differ in size due to swelling or shrinking during the transfer and staining procedures and precise alignment of the replicate blot is difficult (Biotechniques 30, 266, (2001)).

In contrast, fluorescent counterstains have certain common advantages over the colored stains, although the performance characteristics of certain classes of fluorescent counterstains differ substantially. Generally, the fluorescent counterstains that have been described provide a greater linear dynamic range for quantitation and, are easier to visualize on CCD camera-based and laser scanner-based imaging systems. Moreover, they do not interfere with photographic documentation of colored reaction products generated by enzyme-catalyzed detection systems in common use, as the fluorescent counterstains are not visible upon white light illumination, except with particularly abundant proteins. Fluorescent counterstaining of the total protein profiles on nitrocellulose or PVDF membranes has been described using, e.g., 2-methoxy-2,4-diphenyl-2(2H)-furanone (MDPF), SYPRO Rose Plus dye, SYPRO Ruby dye, fluorescamine, fluorescein isothiocyanate (FITC), dichlorotriazinylaminofluorescein (DTAF), and dansyl chloride (Electrophoresis 21, 1123 (2000); BioTechniques 28, 944 (2000)). A method for creating a permanent protein record using MDPF has been used. However, MDPF is not compatible with laser-based gel scanners since it does not absorb significantly in the visible region of the spectrum and its absorbance in the ultraviolet is also less than that of the preferred visible light-excitable dyes of this invention (Electrophoresis 21, 1123 (2000); BioTechniques 28, 944 (2000)). In addition, MDPF-labeled blots must be viewed using wet PVDF membranes, as fluorescence signal decreases 500- fold upon drying (Electrophoresis 19, 2407 (1998)). The fluorescent metal chelate dye, SYPRO Ruby protein blot stain, has been successfully incorporated into immunodetection procedures employing colorimetric, fluorescent or chemiluminescent detection reagents (Anal. Biochem. 276, 129 (1999); Electrophoresis 22, 881 (2001); Electrophoresis 21, 2196, 2208 (2000)). However, staining of immobilized proteins by SYPRO Rose Plus and SYPRO Ruby protein blot stains (both of which only bind noncovalently to proteins) is easily reversible and both dyes are washed away during the blocking step prior to incubation with antibodies. Thus, they do not provide a permanent record of total protein on the blot as do the dyes of this invention. Reactive fluorescent counterstains such as fluorescamine, FITC, DTAF and dansyl chloride have also been used to create a permanent fluorescent protein record (Anal. Biochem. 164, 303 (1987); J. Biochem. Biophys. Methods 46, 31 (2000)). However, these dyes are not very photostable and their fluorescence tends to be environment (dansyl) and/or pH (fluoresceins) sensitive. In addition, the linear range of fluorescence is limited by fluorescence quenching at high concentrations (see Table 3 in Example 28). The current invention allows for a permanent record of both total protein and specific protein(s) with high sensitivity on a single blot and yields significantly greater sensitivity than that of the previously described fluorescent dyes for total protein staining, including the fluorescein-based dyes (see Table 3 in Example 28). Blots can be viewed using standard UV illumination, by illumination with a xenon-arc source or with a dual-wavelength laser-based gel scanner. In particular, all of the preferred dyes of the present invention have absorption maxima at >495 nm and extinction coefficients of >50,000 $cm^{-1}M^{-1}$. Thus, they can be excited by the argonion laser, by longer-wavelength lasers and laser diodes and by other common long-wavelength excitation sources that are typically utilized in the equipment that yields the most sensitive detection of proteins.

The current invention has several distinct advantages over known methods. The current invention uses dipyrromethaneboron difluoride dyes (e.g., various substituted 4-bora-3a,4a-diaza-s-indacene difluoride dyes sold by Molecular Probes, Inc. under the trademark BODIPY) as a counterstain for immobilized poly(amino acids). These dyes have been found to have a variety of advantageous properties, including high extinction coefficients, a high fluorescence quantum yield, spectra that are essentially insensitive to solvent polarity and pH, a narrow emission bandwidth, resulting in a higher peak intensity than other dyes such as fluorescein, a greater photostability than fluorescein in some environments and lack of an ionic charge (U.S. Pat. Nos. 4,774,339; 5,187,288; 5,248,782; U.S. Pat. Nos. 5,274,113; 5,451,663; and MOLECULAR PROBES HANDBOOK OF FLUORESCENT PROBES AND RESEARCH CHEMICALS ("MP HANDBOOK") by Richard P. Haugland, $6^{th}$ Ed., (1996), and its subsequent $7^{th}$ edition and $8^{th}$ edition updates issued on CD Rom in November 1999 and May 2001, respectively, each of which are incorporated by reference). However, it is known that dipyrromethaneboron difluoride dyes, including BODIPY dyes, usually show significant fluorescence quenching when attached to proteins (see, e.g., U.S. Pat. No. 5,719,031; MP HANDBOOK, supra, $6^{th}$ edition at p. 14; and Anal Biochem 251, 144 (1997)), particularly when proteins are labeled with a large molar excess of the reactive dipyrromethaneboron difluoride dye. Unexpectedly, it was found that certain dipyrromethaneboron difluoride dyes that are used to label proteins or other poly(amino acids) immobilized on a solid surface do not suffer from this reported quenching phenomenon. Unexpectedly, this severe quenching was not observed in the present invention when the proteins were detected following blotting onto a membrane, even when the proteins were reacted with a vast excess of the reactive dye. In addition, in contrast to colorimetric counterstaining methods, the current invention permits simultaneous dichromatic visualization of a target protein and the remaining proteins in the profile on a single electroblot. Since the selected dipyrromethaneboron difluoride counterstains also absorb significantly in the UV region of the spectrum, blots can be visualized using a handheld UV lamp or a UV-epi-illumination system in conjunction with a photographic or CCD camera. These counterstains also absorb in the visible region of the spectrum, and they may be detected with a dual-wavelength laser-based gel scanner using a photomultiplier tube. Unlike some other reactive dyes that have been used to detect proteins on a solid support, the blots can be imaged either wet or dry, as the selected dipyrromethaneboron difluoride counterstains do not fade upon drying. Furthermore, the use of dipyrromethaneboron difluoride counterstains does not interfere with the subsequent methods commonly used to analyze immobilized proteins.

Thus, there is an unmet need for an easy to use and sensitive method for the labeling and detection (and optionally quantitation) of total proteins and other poly(amino acids) on membranes and other solid supports, that would overcome the disadvantages and limitations of current methods. Such methods would be useful in research, forensics, quality control and medical diagnostics. This invention meets these and other needs.

SUMMARY OF THE INVENTION

Poly(amino acids) that are immobilized on a solid support are labeled according to the present invention by incubating the poly(amino acids) with a labeling mixture that comprises one or more chemically reactive dipyrromethaneboron difluoride dyes for a time sufficient for the dye to form a covalent bond with the poly(amino acids), and then removing any unbound dye by washing the immobilized poly(amino acids) with a suitable solvent. Typically, the solid support is made of solvent-resistant materials such as nylon, poly(vinylidene difluoride) (PVDF), glass, plastic, and their derivatives. The immobilized poly(amino acids) generally have a molecular weight between 500 and 200,000 daltons. For best results, the dye is present in the labeling mixture in a concentration of 0.01 micromolar to 10 micromolar. Subsequent addition of a specific binding pair member that binds selectively to a target or targets within the sample of immobilized poly(amino acids) is a preferred aspect of the invention.

In one aspect of the invention, the poly(amino acids) are separated by gel electrophoresis prior to being transferred to a solid support for labeling with the dipyrromethaneboron difluoride dyes. In another aspect of the invention, the poly(amino acids) are immobilized in arrays on the solid support for labeling with the dipyrromethaneboron difluoride dyes. In yet another aspect of the invention, the poly(amino acids) are immobilized by being selectively bound to their specific aptamers arrayed on a solid support.

After the immobilized poly(amino acids) are labeled with the dipyrromethaneboron difluoride dyes, whether blotted from a gel or formatted in arrays, the unbound dye is removed (typically by washing, e.g., with a solvent) and the labeled poly(amino acids) are detected by illuminating the bound dipyrromethaneboron difluoride dyes to yield a detectable optical response, typically a fluorescent optical response, and using the detectable optical response to detect the corresponding poly(amino acids). Dipyrrometheneboron difluoride dyes having an excitation peak between 495 nm and 640 nm are particularly useful for the invention. In one aspect of the invention, following reaction with the immobilized proteins and washing to remove unconjugated dyes, the protein conjugates are illuminated for 5 seconds or less.

In one aspect of the invention, the proteins or other poly(amino acids) are bound to aptamers that are, in turn, previously arrayed on a solid support. Aptamers can be used as a diagnostic or prognostic tool. In one embodiment, arrays of aptamers are bound to a solid support, and a protein sample is applied. Unbound protein is washed off, and dipyrrometheneboron difluoride dyes that covalently label reactive sites in proteins but not nucleic acids are used to generate protein profiles. The labeled proteins on aptamers are detected by using an array reader, which uses the same light sources as are commonly used in commercially available blot readers.

In aspects of the invention that include adding a specific binding pair member that binds selectively to a target or targets within the immobilized poly(amino acids), the specific binding pair member is typically a lectin, a biotin-binding protein, an antibody or an antibody fragment. In one aspect of the invention, a label is covalently attached to the specific binding pair member. Alternatively, the specific binding pair member is unlabeled, but a secondary binding pair member is added, to which secondary binding pair member a label is covalently attached and which secondary binding pair member binds selectively to the specific binding pair member (e.g., the secondary binding pair member is a secondary antibody and the specific binding pair member is a primary antibody). The label on the secondary binding pair member or specific binding pair member is typically a fluorescent dye, a biotin, a hapten such as digoxigenin, or an enzyme (e.g., a peroxidase, luciferase, aequorin, glycosidase or phosphatase). Where the label is an enzyme, a fluorogenic or chemiluminescent substrate (e.g., a fluorescent tyramide, a polyfluorinated xanthene, a fluorogenic quinazolinone, DDAO phosphate, luciferin, coelenterazine or a dioxetane phosphate) is typically added for detection of the target. Where the target of the specific binding pair member is a biotinylated protein, a biotin-binding protein (e.g., an avidin) to which a label is covalently attached is used for detection of the target. Where the label is a hapten that is not biotin, an antibody to that hapten is utilized in the detection scheme, for instance if the hapten is digoxigenin the specific binding pair member comprises an antibody to digoxigenin. Unbound specific binding pair members or secondary binding pair members are removed for best detection results.

In one further aspect of the invention, the specific binding pair member is a chemical stain such as a thiol-reactive dye that recognizes only those proteins that contain thiols, a dye that selectively reacts with oxidized glycoproteins such as Pro-Q Emerald 300 (U.S. patent Ser. No. 09/970,215) or Pro-Q Sapphire 365 or Pro-Q Sapphire 488 oligohistidine stains (Molecular Probes, Inc).

In a further embodiment of the invention, kits adapted for the practice of any of the claimed methods are described. Such kits typically include one or more dipyrrometheneboron difluoride dyes and one or more specific binding pair members or secondary binding pair members to which a label is covalently attached. Where the label is an enzyme that is capable of utilizing a fluorogenic, chromogenic or chemiluminescent substrate, the appropriate fluorogenic, chromogenic or chemiluminescent substrate is included.

The methods of the invention are broadly applicable to labeling any poly(amino acid) from any origin. The methods are especially useful and applicable to labeling poly(amino acids) from biological material. Such poly(amino acids) may be contained in cells or cellular materials and will typically be obtained for the purposes of immunoassaying to determining the presence or location of a specific target, diagnosing medical conditions, or identifying disease states. These and other aspects of the invention are described in more detail below.

DESCRIPTION OF THE SPECIFIC EMBODIMENTS

In the present invention, a novel method of labeling and/or detecting immobilized poly(amino acids) is disclosed, and novel kits for practicing such methods are provided. To facilitate understanding of the invention, the disclosure of the invention is organized in sections, as follows. First, a definition section is provided to define terms and phrases used commonly throughout the disclosure. This definition section includes a comprehensive description of the types of immobilized poly(amino acids), solid supports, and labeled specific binding pair members that can be used with the invention. The next section describes specific dipyrrometheneboron difluoride dyes used in labeling the poly(amino acids) in methods of the invention. The following section describes methods of the invention for labeling or detecting immobilized poly(amino acids). This next section is a description of the kits adapted for practicing the methods of the invention. Then various applications and expansions of the invention are described; this description is followed by detailed examples illustrating the invention.

Definitions

To assist in the understanding of the invention, the following terms, as used herein, are defined below.

"Aptamer" means a nucleic acid that binds selectively to an intended target molecule ("target," as defined below). This binding interaction does not encompass standard nucleic acid/nucleic acid hydrogen bond formation exemplified by Watson-Crick base pair formation (e.g., A binds to U or T and G bind to C), but encompasses all other types of noncovalent (or in some cases covalent) binding. Non-limiting examples of non-covalent binding include hydrogen bond formation, electrostatic interaction, Van der Waals interaction and hydrophobic interaction. An aptamer may bind to another molecule by any or all of these types of interaction, or in some cases by covalent interaction. Covalent binding of an aptamer to another molecule may occur where the aptamer or target molecule contains a chemically reactive or photoreactive moiety. The term "aptamer" or "specifically binding nucleic acid" refers to a nucleic acid that is capable of forming a complex with an intended target substance. "Target-specific" means that the aptamer binds to a target analyte with a much higher affinity than it binds to contaminating materials.

"Array" means a two-dimensional spatial grouping or an arrangement of biomolecules.

"Binding pair" refers to first and second molecules that bind selectively to each other. A specific binding pair member is the first member of the binding pair, and binds selectively to the second member of the binding pair, which is its complement or complementary binding pair member. The binding between the members of a binding pair is typically noncovalent.

"Binding selectively" refers to the situation in which one member of a specific intra or inter species binding pair will not show any significant binding to molecules other than its specific intra or inter species binding partner (e.g., an affinity of about 100-fold less). Binding is mediated through hydrogen bonding or other molecular forces.

"Detectable label" or "Label" means a chemical used to facilitate identification and/or quantitation of a target substance. Illustrative labels include labels that can be directly observed or measured or indirectly observed or measured. Such labels include, but are not limited to, radiolabels that can be measured with radiation-counting devices; pigments, dyes or other chromogens that can be visually observed or measured with a spectrophotometer; chemiluminescent labels that can be measured by a photomultiplier-based instrument or photographic film, spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems, for example. The label can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate or a spontaneously chemiluminescent product from a suitable precursor. The term label can also refer to a "tag" or hapten that can bind selectively to a labeled molecule such that the labeled molecule, when added subsequently, is used to generate a detectable signal. For instance, one can use biotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex Gold reagent, or a fluorescent tyramide (Molecular Probes, Inc.) to detect the presence of HRP. In a similar fashion, the tag can be a hapten or antigen (e.g., digoxigenin or an oligohistidine), and an enzymatically, fluorescently, or radioactively labeled antibody can be used to bind to the tag. Numerous labels are known by those of skill in the art and include, but are not limited to, microparticles, fluorescent dyes, haptens, enzymes and their chromogenic, fluorogenic and chemiluminescent substrates and other labels that are described in the MOLECULAR PROBES HANDBOOK OF FLUORESCENT PROBES AND RESEARCH CHEMICALS by Richard P. Haugland, 6$^{th}$ Ed., (1996), and its subsequent 7$^{th}$ edition and 8$^{th}$ edition updates issued on CD Rom in November 1999 and May 2001, respectively, the contents of which are incorporated by reference, and in other published sources.

"Counterstain" (as a verb) means to label all or substantially all of the poly(amino acids) that are present in the immobilized poly(amino acids).

"Counterstain" (as a noun) means a reagent or combination of reagents that labels all or substantially all of the poly(amino acids) that are present in the immobilized poly (amino acids).

"Detectable response" means a change in, or occurrence of, a signal that is detectable either by observation or instrumentally. Typically the detectable response is an optical response resulting in a change in the wavelength distribution patterns or intensity of absorbance or fluorescence or a change in light scatter, fluorescence lifetime, fluorescence polarization, or a combination of the above parameters. Other detectable responses include, for example, chemiluminescence, phosphorescence, radiation from radioisotopes, attraction to a magnet and electron density.

"Dipyrromethenoboron difluoride reactive dyes" means any of chemically reactive derivatives of the dyes described in U.S. Pat. Nos. 4,774,339; 5,187,288; 5,248,782; 5,274,113; and 5,451,663 that have an absorption maximum below 640 nm. Many dipyrrometheneboron difluoride reactive dyes are commercially available under the trademark BODIPY (Molecular Probes, Inc.).

"Chemically reactive derivatives" means those dye derivatives that covalently label materials under mild conditions.

"Chemiluminescent substrate" is defined as any compound which enters into a chemical reaction with a peroxide or a phosphatase component to produce chemiluminescence. Typically chemiluminescence is initiated upon an event, such as cleavage of a bond which generates an unstable intermediate that fragments and releases light or a photon as part of the high-energy state decay process (U.S. Pat. Nos. 4,931,223 and 4,962,192).

"Gel electrophoresis" as used herein, refers to a variety of gels that may be used in the technique of gel electrophoresis and includes gels formed by a variety of gel matrix materials, including polyacrylamide, agarose, polyacrylamide-agarose composites, and the like. It also encompasses the net migration of a solute under the influence of an electric field by the combined effects of electroosmosis and electrophoresis. It further includes any non-denaturing cathodic or anodic electrophoresis, including sodium dodecyl sulfate (SDS)-gel electrophoresis, isoelectric focusing and gradient gels.

"Enzyme" means a protein molecule produced by living organisms, or through chemical modification of a natural protein molecule, that catalyses chemical reactions of other substances without itself being destroyed or altered upon completion of the reactions. Examples of other substances, include but are not limited to chemiluminescent, chromogenic, or fluorogenic substances.

The term "fluorescent substrate" is used to describe a substrate that will produce a fluorescent product upon modification.

"Immobilized" means attached to or operatively associated with an insoluble and/or dehydrated substance or solid phase that comprises or is attached to a solid support.

"Kit" means a packaged set of related components, typically one or more compounds or compositions.

"Poly(amino acid)" refers to various natural or synthetic compounds containing molecules of amino acids of one or more amino substituents linked by the carboxyl group of one amino acid and the amino group of another, including but not limited to proteins, polypeptides, glycoproteins, etc. Poly(amino acids) comprise one or more a targets to which an antibody, lectin, aptamer, protein-detection reagent, or other similar specific binding pair member can bind. Typically, the sample from which poly(amino acids) are selected for analysis comprises tissue, a cell or cells, cell extracts, cell homogenates, purified or reconstituted proteins, recombinant proteins, bodily and other biological fluids, viruses or viral particles, prions, subcellular components or synthesized proteins. Possible sources of cellular material for such samples include without limitation plants, animals, fungi, protists, bacteria, archae, or cell lines derived from such organisms, including animal cells or animal cell lines that are normal or diseased.

"Selective protein-staining techniques" means to generate one or more separately detectable signals for a specific target within the immobilized poly(amino acid) sample.

"Solid support" means a substrate material having a rigid or semi-rigid surface. Typically, at least one surface of the substrate will be substantially flat, although it may be desirable to physically separate certain regions with, for example, wells, raised regions, etched trenches, or other such topology. Solid support materials also include spheres (including microspheres), rods (such as optical fibers) and fabricated and irregularly shaped items. Solid support materials include any materials that are used as affinity matrices or supports for chemical and biological molecule syntheses and analyses, such as, but are not limited to: poly(vinylidene difluoride) (PVDF), polystyrene, polycarbonate, polypropylene, nylon, glass, dextran, chitin, sand, pumice, polytetrafluoroethylene, agarose, polysaccharides, dendrimers, buckyballs, polyacrylamide, Kieselguhr-polyacrylamide non-covalent composite, polystyrene-polyacrylamide covalent composite, polystyrene-PEG [poly(ethylene glycol)] composite, silicon, rubber, and other materials used as supports for solid phase syntheses, affinity separations and purifications, hybridization reactions, immunoassays and other such applications. The solid support may be particulate or may be in the form of a continuous surface, such as a microtiter dish or well, a glass slide, a silicon chip, a nitrocellulose sheet, nylon mesh, or other such materials.

"Solvent resistant material" means a solid support that is insoluble and inert to solvents commonly utilized in the field of proteomics. The solid support would preferably be inert to solvents that include but are not limited to dimethylformamide, methanol, ethanol, propanol, methylene chloride and N-methyl-2-pyrrolidone.

"Target" means a substance of analytical interest that is analytically distinguishable from its surrounding environment.

"Washing" means contacting a material with a solution to remove or dilute a composition introduced in a previous step. Washing solutions are typically pure solvents or mixtures of solvents, optionally with salts or pH-modifying agents that solubilize and/or rinse away some or all of the composition introduced in the previous step.

Selection of Dipyrromethenboron Difluoride Dyes

In this method, immobilized poly(amino acids) are labeled by incubating the immobilized poly(amino acids) with a labeling mixture that comprises a reactive dipyrromethenboron difluoride dye. An extensive assortment of dipyrromethenboron difluoride dyes and the effects of various substituents on their spectral properties have been described previously (U.S. Pat. Nos. 4,774,339; 5,274,113; 5,187,288; 5,248,782; 5,338,854 and 5,433,896, all incorporated by reference). These dyes differ in their absorption and emission wavelengths; however, the preferred dyes have substituents that yield dyes with absorption maxima between 495 nm and 640 nm and extinction coefficients >50,000 $cm^{-1}M^{-1}$.

In one aspect of the invention, the dipyrromethenboron difluoride dyes have the formula:

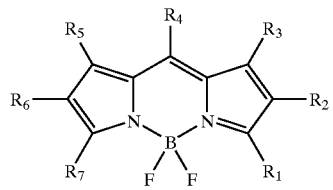

wherein each of $R^1$ through $R^7$ are independently selected from the group consisting of H, halogen, L—Rx, and $C_1$-$C_6$ alkyl, aryl, arylethenyl, arylbutadienyl, and heteroaryl. By alkyl is meant a saturated hydrocarbon chain that is optionally further substituted by carboxylic acid, sulfonic acid, or halogen. By aryl is mean an unsaturated 5- or 6-membered hydrocarbon ring. By heteroaryl is meant an unsaturated 5- or 6-membered ring that contains one or two heteroatoms. Each aryl or heteroaryl ring is optionally further substituted by $C_1$-$C_6$ alkyl, $C_1$-$C_6$ perfluoroalkyl, cyano, halogen, azido, carboxylic acid, sulfonic acid, or halomethyl. For the preferred dyes, one or more of $R^1$ through $R^7$ is H, two or more of $R^1$ through $R^7$ is nonhydrogen, and only one of $R^1$ through $R^7$ is —L—Rx. The element L is a spacer having 1–24 nonhydrogen atoms selected from the group consisting of C, N, O, P, and S and is composed of any combination of single, double, triple or aromatic carbon—carbon bonds, carbon-nitrogen bonds, nitrogen—nitrogen bonds, carbon-oxygen bonds, carbon-sulfur bonds, phosphorus-oxygen bonds, and phosphorus-nitrogen bonds. The element Rx is a reactive group that is a maleimide or a succinimidyl ester of a carboxylic acid. In one aspect, —L—Rx is at $R^1$. In another aspect, —L—Rx is at $R^2$. In yet another aspect, —L—Rx is at $R^4$. In yet another aspect, $R^1$ is methyl or —L—Rx. In a further aspect, $R^2$ is H, bromine, or —L—Rx. Typically, $R^3$ is H or methyl. Typically, $R^4$ is H or —L—Rx; In preferred embodiments, $R^5$ is H, methyl or phenyl. Typically, $R^6$ is H or bromine. In preferred embodiments, $R^7$ is methyl, phenyl, alkoxyphenyl, phenylethenyl, phenylbutatdienyl pyrrolyl, or thienyl. Preferred embodiments of —L are where —L— is —$(CH_2)_2$—, —$(CH_2)_4$—, —$OCH_2C(O)NH(CH_2)_5$—, —$(CH_2)_2$—C(O)NH$(CH_2)_5$—, or —$(CH)_2C_6H_4OCH_2C(O)NH(CH_2)_5$—. Preferably, Rx is a succinimidyl ester of a carboxylic acid.

Dipyrromethenboron difluoride dyes that are halogenated are not preferred since halogenation has been shown to reduce the fluorescence yield of the dye. Dipyrromethenboron difluoride dyes that are substituted at positions 1, 2, 3, 5, 6, and 7 only by hydrogen atoms or alkyl groups tend to have green to yellow-green fluorescence and are optimally excited by the 488-nm spectral line of the argon-ion laser. Substitution of dipyrromethenboron difluoride dyes by alkenyl, polyalkenyl, aryl and heteroaryl moieties or combinations of these substituents causes a red-shift of both the absorption and emission maxima of the fluorophore, permitting use of the dyes alone or in combination with other labels that have contrasting optical properties.

In a preferred embodiment, the dipyrromethenboron difluoride reactive dye is an amine-reactive dye since aliphatic amines are common to most or all proteins. In a more preferred embodiment, the dipyrromethenboron difluoride is a succinimidyl ester and, in the most preferred embodiments the succinimidyl ester is separated from the fluorophore by an additional seven-atom aminohexanoyl ("X") spacer. A number of chemically reactive dipyrromethenboron dyes are commercially available under the trademark BODIPY® dyes, presently including all of those listed in Table 1. Properties of these dyes are described by Haugland, HANDBOOK OF FLUORESCENT PROBES AND RESEARCH CHEMICALS ($6^{th}$ Ed. Molecular Probes, Inc., Eugene, Oreg., 1996), which is incorporated by reference. Example 29 provides the procedure used to screen the dyes represented in Table 1 for their suitability for detecting total-protein content on a blot.

TABLE 1

Reactive dipyrromethreneboron difluoride dyes that are preferred for this invention.

| Dipyrromethreneboron difluoride reactive dyes | Commercial Product* |
|---|---|
| 6-((4,4-difluoro-5,7-dimethyl-4-bora-3a,4a-diaza-s-indacene-3-propionyl)amino)hexanoic acid, succinimidyl ester | BODIPY FL-X, SE |
| 6-((4,4-difluoro-1,3-dimethyl-5-(4-methoxyphenyl)-4-bora-3a,4a-diaza-s-indacene-2-propionyl)amino)hexanoic acid, succinimidyl ester | BODIPY TMR-X, SE |
| 6-(((4-(4,4-difluoro-5-(2-thienyl)-4-bora-3a, 4a-diaza-s-indacene-3-yl)phenoxy)acetyl)amino) hexanoic acid, succinimidyl ester | BODIPY TR-X, SE |
| 6-((4,4-difluoro-5-phenyl-4-bora-3a,4a-diaza-s-indacene-3-propionyl)amino)hexanoic acid, succinimidyl ester | BODIPY R6G-X, SE |
| 4,4-difluoro-5-phenyl-4-bora-3a,4a-diaza-s-indacene-3-propionic acid, succinimidyl ester | BODIPY R6G, SE |
| 6-(((4,4-difluoro-5-(2-thienyl)-4-bora-3a,4a-diaza-s-indacene-3-yl)styryloxy)acetyl)amino-hexanoic acid, succinimidyl ester | BODIPY 630/650-X, SE |
| 4,4-difluoro-5,7-diphenyl-4-bora-3a,4a-diaza-s-indacene-3-propionic acid, succinimidyl ester | BODIPY 530/550, SE |
| 4,4-difluoro-5-(2-thienyl)-4-bora-3a,4a-diaza-s-indacene-3-propionic acid, succinimidyl ester | BODIPY 558/568, SE |
| 4,4-difluoro-5-styryl-4-bora-3a, 4a-diaza-s-indacene-3-propionic acid, succinimidyl ester | BODIPY 564/570, SE |
| 4,4-difluoro-5-(2-pyrrolyl)-4-bora-3a,4a-diaza-s-indacene-3-propionic acid, succinimidyl ester | BODIPY 576/589, SE |
| 4,4-difluoro-5-(4-phenyl-1,3-butadienyl)-4-bora-3a,4a-diaza-s-indacene-3-propionic acid, succinimidyl ester | BODIPY 581/591, SE |
| 4,4-difluoro-1,3,5,7-tetramethyl-4-bora-3a, 4a-diaza-s-indacene-8-propionic acid, succinimidyl ester | BODIPY 493,503, SE |
| 4,4-difluoro-5,7-dimethyl-4-bora-3a, 4a-diaza-s-indacene-3-pentanoic acid, succinimidyl ester | BODIPY FL C5, SE |
| 6-(((4,4-difluoro-5-(2-pyrrolyl)-4-bora-3a, 4a-diaza-s-indacene-3-yl)styryloxy)acetyl)amino-hexanoic acid, succinimidyl ester | BODIPY 650/665-X, SE |
| 2,6-dibromo-4,4-difluoro-5,7-dimethyl-4-bora-3a, 4a-diaza-s-indacene-3-propionic acid, succinimidyl ester | BODIPY FL Br$_2$, SE |
| 4,4-difluoro-5,7-dimethyl-4-bora-3a,4a-diaza-s-indacene-3-propionic acid, succinimidyl ester | BODIPY FL, SE |

*Available as of the filing date from Molecular Probes, Inc., www.probes.com.

The dipyrromethreneboron difluoride dye concentration in the labeling mixture is typically between 1 μM and 100 μM, preferably between about 5 μM and about 20 μM; more preferably at least 10 μM.

The synthesis of dipyrromethreneboron difluoride dyes is well documented in U.S. Pat. Nos. 4,774,339; 5,274,113; 5,187,288; 5,248,782; 5,338,854 and 5,433,896, all incorporated by reference, and other publications. Many dyes useful for the invention are available from Molecular Probes, Inc. (Eugene, Oreg.).

The dipyrromethreneboron difluoride dye-labeled immobilized poly(amino acid) are illuminated to give an optical response that is a fluorescence emission (fluorescence response). Illumination is by a light source capable of exciting the dipyrromethreneboron difluoride dye-poly (amino acid) complex, typically at or near the wavelength of an absorption maximum, such as an ultraviolet (254–370 nm) or visible (495–640 nm) wavelength emission lamp, an arc lamp, a laser, or even sunlight or ordinary room light. Preferably, the sample is excited with a wavelength within 20 nm of the maximum absorption of the dipyrromethreneboron difluoride dye-poly(amino acid) conjugate.

Preferably, the dipyrromethreneboron difluoride dye-poly (amino acid) complexes possess an absorption maximum between 480 and 650 nm, more preferably between 495 and 640 nm, most preferably matching the wavelength of a laser-based illumination source. The complexes also preferably excite with some efficiency in the UV at or near 300 nm.

Methods of the Invention

The methods of the invention use chemically reactive dipyrromethreneboron difluoride dyes to accomplish counterstaining poly(amino acids) that are supported of a solid support, wherein the solid supports include but are not limited to PVDF, nitrocellulose, polystyrene, glass and solid supports used in microarray and aptamer technologies. In one aspect of the invention, the counterstain is used in conjunction with selective protein-staining techniques to generate one or more separately detectable signals.

In one embodiment, the method of labeling immobilized poly(amino acids) with dipyrromethreneboron difluoride dyes comprises the steps of:
 a. separating poly(amino acids) by gel electrophoresis
 b. transferring said separated poly(amino acids) to a solid support, resulting in immobilized poly(amino acids)
 c. combining said immobilized poly(amino acids) on said solid support with a labeling mixture that comprises one or more dipyrromethreneboron difluoride dyes for a sufficient time for the dyes to form a covalent bond with said poly(amino acids).

The method optionally comprises a step to remove excess and unreacted dipyrromethreneboron difluoride dye. Typically, the excess unreacted dye and any of its decomposition products are removed by washing.

The poly(amino acids) that are suitable for staining using this method include both synthetic and naturally occurring poly(amino acids), comprising both natural and unnatural amino acids. The poly(amino acids) of the invention include peptides, polypeptides and proteins. Poly(amino acids) that are labeled and analyzed according to the present method optionally incorporate non-peptide regions (covalently or non-covalently) including lipid (lipopeptides and lipoproteins), phosphate (phosphopeptides and phosphoproteins), and/or carbohydrate (glycopeptides and glycoproteins) regions; or incorporate metal chelates or other prosthetic groups or non-standard side chains; or are multi-subunit complexes, or incorporate other organic or biological substances, such as nucleic acids or cofactors. The poly(amino acids) are optionally relatively homogeneous or heterogeneous mixtures of poly(amino acids). Typically, the poly (amino acids) are proteins.

In one embodiment of the invention, the poly(amino acids) are immobilized on a membrane, such as a poly (vinylidene difluoride) (PVDF) membrane, wherein the poly (amino acids) are applied to the membrane by blotting, spotting, electroblotting or other methods.

In one embodiment of the invention, separated poly (amino acids) in electrophoretic gels are transferred to a filter membrane or blot or other solid or semi-solid matrix before being combined with the labeling mixture. The present method is effective for both denaturing and non-denaturing gels. Denaturing gels optionally include a detergent such as SDS or other alkyl sulfonate (e.g., 0.05%–0.1% SDS). Typically, polyacrylamide or agarose gels are used for electrophoresis. Commonly used polyacrylamide gels include but are not limited to Tris-glycine, Tris-tricine, mini- or full-sized gels. Agarose gels include modified agaroses. Alternatively, the gel is an isoelectric focusing gel or strip. In addition to polyacrylamide and agarose gels, suitable electrophoresis gels are optionally prepared using other polymers, such as HYDROLINK. Alternatively, the electrophoretic gel is a gradient gel. Useful electrophoretic gels for the present invention are either prepared according to standard procedures or are purchased commercially.

In another embodiment of the method a specific binding pair member that binds selectively to its complementary member is used to detect a target or targets within the poly(amino acids) that is the complementary member. Typically, the specific binding pair member contains a label, such that when the binding pair member selectively binds to its complementary member, it forms a label-specific binding pair-target complex. In one aspect, the specific binding pair member is covalently labeled with an enzyme, and the enzyme is capable utilizing a chromogenic, fluorogenic or chemiluminescent substrate to generate a detectable optical response. The specific binding pair member that is covalently labeled with an enzyme then selectively binds to the target/complementary member to form an enzyme-specific binding pair-target complex.

In general, an enzyme-mediated technique use an enzyme labeled attached to one member of a binding pair or series of binding pairs as a reagent to detect the complimentary member of the pair or series. In the simplest case, only the members of one binding pair are used. One member of the specific binding pair is the analyte, i.e. substance of analytical interest. An enzyme is attached to the other (complimentary) member pair, forming a complimentary complex. The complimentary conjugate attaches to its complimentary analyte to form a complimentary binding complex. The complimentary binding complexes include but are not limited to, antibody-antigen interaction, avidin (streptavidin and derivatives thereof) and biotin (including desthiobiotin and iminobiotin), lectins and carbohydrates, immunoglobulins and protein A, G, L or hybrids thereof. Examples 1–5, 8–10, and 15–22 provide experimental procedures for these methods but these techniques are well known to one skilled in the art.

Alternatively, multiple binding pairs may be sequentially linked to the target complement in the poly(amino acids), the specific binding pair member, or to both, resulting in a series of specific binding pairs interposed between the target and the detectable enzyme label of the specific binding pair member. Example 23–25 provides a typical procedure for the use of multiple binding pairs.

In a preferred embodiment of this method, an amine-reactive dipyrromethenboron difluoride dye selected from Table 2 is used as a general protein detection reagent. Optionally an enzyme label on a specific binding pair member that is capable of utilizing a fluorogenic, chromogenic or chemiluminescent substrate to generate a detectable optical response is used to detect a specific immobilized protein or proteins. In a preferred embodiment the enzyme substrate is a fluorogenic substrate; in the most preferred embodiments the enzyme substrate yields a detectable fluorescent product at or near the site of binding of the specific binding pair member to the specific immobilized protein or proteins. In one embodiment, the enzyme is alkaline phosphatase or horseradish peroxidase. In a further embodiment, the alkaline phosphatase or horseradish peroxidase is covalently bound to an antibody to mouse IgG or to rabbit IgG or to a lectin. In a further embodiment, the fluorogenic substrate is 9H-(1,3-dichloro-9,9-dimethylacridin-2-one-7-yl) phosphate (DDAO phosphate), a polyfluorinated xanthine (U.S. Pat. No. 6,162,931, incorporated by reference), a 2-(2'-phosphoryloxyphenyl)-4(3H)-quinazolinone derivative such as ELF 97 phosphate or ELF 39 phosphate (U.S. Pat. No. 5,443,986, incorporated by reference) or a tyramide (U.S. Pat. Nos. 5,196,306; 5,583,001 and 5,731,158, which are incorporated by reference). The quinazolinone derivatives are commercially available from Molecular Probes, Inc. under the trademark ELF®. In a further embodiment the peroxidase substrate is an Alexa Fluor, Oregon Green, Marina Blue or biotin-XX tyramide (Molecular Probes, Inc.). In an additional embodiment, the chemiluminescent substrate is the BOLD substrate (Intergen), Fluoroblot substrate (Pierce Chemical), ECL® substrates (Amersham Biosciences) or CSPD® substrates (Applied Biosystems).

The fluorogenic quinazolinone substrates are combined with the enzyme-specific binding-pair target-complex under conditions suitable for the formation of a precipitate. Several variations of fluorogenic quinazolinone substrates are suitable for this invention, including ELF 97 and ELF 39 phosphates, blot of which are described in U.S. Pat. No. 5,443,986, which is incorporated by reference and are commercially available, as described in the MOLECULAR PROBES HANDBOOK OF FLUORESCENT PROBES AND RESEARCH CHEMICALS by Richard P. Haugland, $6^{th}$ Ed., (1996), and its subsequent $7^{th}$ edition and $8^{th}$ edition updates issued on CD Rom in November 1999 and May 2001, respectively, the contents of which are incorporated by reference, and in other published sources. Examples 4, 5, 23, 24, 25 and 32 contain methods relating to the use of quinazolinone derivatives as a substrate.

The fluorogenic substrate DDAO phosphate is combined with the enzyme-specific binding-pair target-complex under conditions suitable for formation of the precipitate. The DDAO phosphate substrate (U.S. Pat. No. 4,810,636) is described in the MOLECULAR PROBES HANDBOOK OF FLUORESCENT PROBES AND RESEARCH CHEMICALS by Richard P. Haugland, $6^{th}$ Ed., (1996), and its subsequent $7^{th}$ edition and $8^{th}$ edition updates issued on CD Rom in November 1999 and May 2001, respectively, the contents of which are incorporated by reference, and in other published sources. Examples 1–3, 19, 21–22 and 29–30 describe methods for DDAO phosphate use and detection.

The fluorogenic tyramide substrates are combined with the horseradish peroxidase-labeled, specific binding pair-labeled target-complex under conditions suitable for the formation of an immobilized product. The use of labeled tyramides is described in U.S. Pat. Nos. 5,196,306 and 5,583,001, the contents of which are incorporated by reference, and in other published sources. Examples 15 describes a method for use and detection of fluorgenic tyramide substrates.

In another embodiment of the method, the specific binding pair member is covalently labeled with a fluorescent dye. The specific binding pair member selectively binds to its complementary member/target, to form a fluorescent dye-specific binding-pair target-complex. The fluorescent dye is detectably distinct from the dipyrromethenboron difluoride dye used to counterstain the immobilized poly(amino acids) but may be a dipyrromethenboron difluoride dye of a different chemical structure. Preferably, however, the fluorescent dye is a xanthene, including fluorescein- and rhodamine-based dyes or is a carbocyanine, including Cy3 and Cy5 dyes.

In one aspect of the invention, stained solid supports are used to analyze the composition of complex sample mixtures and additionally to determine the relative amount of a particular poly(amino acid) in such mixtures. Stained solid supports are also used to estimate the purity of isolated poly(amino acids) and to determine the degree of proteolytic degradation of the immobilized poly(amino acids). In addition, electrophoretic mobility is optionally used to provide a measure of the molecular weight of uncharacterized poly (amino acids) and to analyze subunit composition for multi-subunit poly(amino acids), as well as to determine the stoichiometry for the subunits bound in such proteins. In the case of isoelectric focusing electrophoresis (IEF), electrophoretic mobility is used to provide a measure of the net molecular charge possessed by the poly(amino acid).

The two-dimensional electrophoresis portion of the method of this invention can be performed according to known procedures, which may vary widely. In a typical procedure, the sample is first given a linear separation in an elongate or rod-shaped gel, with an electric potential imposed along the length of the gel. Migration and separation thus occur along the gel axis until the proteins in the sample are distributed among zones positioned along the length of the gel. This is followed by placement of the elongate gel along one edge of a slab gel, and the imposition of an electric potential in a direction lying within the plane of the slab gel and perpendicular to the edge where the elongate gel is placed. The proteins from each zone of the elongate gel migrate into the slab gel in the direction transverse to the axis of the elongate gel. The result is a two-dimensional array of protein spots in the slab gel. By using one mode of separation or one set of separation conditions in the first dimension (the elongate gel) and a different mode or set of separation conditions in the second dimension (the slab gel), highly effective separations can be obtained. For example, the first mode may be one based on charge, such as isoelectric focusing, and the second may be based on molecular weight.

Alternatively, the two dimensions of the separation may be based on the same parameter but may differ in the compositions of the two gels. The two gels may differ in gel concentration or chemical components. As a further alternative, the two dimensions of the separation may be based on the same parameter and performed in gels of the same composition and concentration, but differ in a separation condition, such as a stepwise difference in pH, for example. Still further alternatives are the use of a homogeneous gel in one of the two dimensions and a gradient gel in the other, the use of two different protein solubilizers in the two dimensions, or two different concentrations of the same protein solubilizer, and the use of a nonchanging buffer system in one dimension and a changing (gradient, for example) buffer system in another dimension.

Transfer of poly(amino acids) from a gel onto a solid surfaces like a membranes can be carried out using several methods such as a vacuum, capillary action or by means of an electric field (electroblotting).

Poly(amino acids) may be obtained from various sources, including biological fermentation media and automated protein synthesizers, as well as prokaryotic cells, eukaryotic cells, virus particles, tissues, and biological fluids. Suitable biological fluids include, but are not limited to, urine, cerebrospinal fluid, blood, lymph fluids, interstitial fluid, cell extracts, mucus, saliva, sputum, stool, physiological or cell secretions or other similar fluids. In one embodiment, the poly(amino acids) comprise the proteome of an animal cell, typically a mammalian cell.

One aspect of the invention comprises separation of the poly(amino acids) from the electrophoretic matrix. Another aspect of the invention further comprises ionization of the poly(amino acids) and their characterization by mass spectroscopy, or transfer and subsequent analysis of the poly (amino acids) by Edman sequencing.

A further embodiment of the invention is a method of detecting poly(amino acids) comprising the steps of:
a. combining a poly(amino acids) immobilized on a solid support with a labeling mixture that comprises one or more dipyrrometheneboron difluoride dyes and
b. incubating a labeling mixture for a sufficient time to form a covalent bond between the dipyrrometheneboron difluoride dyes and the immobilized poly(amino acids) to form a dye poly(amino acid) complex;
c. removing any unbound dipyrrometheneboron difluoride dyes;
d. illuminating the dye-poly(amino acid) complex to yield a detectable optical response;
e. using the detectable optical response to detect the corresponding dye-poly(amino acid) complex.

In one aspect of this method, the poly(amino acids) are immobilized on a membrane. The immobilized poly(amino acids) are typically on a membrane or in an array. In another aspect, the poly(amino acids) are selectively bound to a corresponding aptamer, which aptamers are immobilized.

In the subject arrays and aptamers, the poly(amino acids) are immobilized to the surface of a solid support. By immobilized is meant that the poly(amino acids) maintain their position relative to the rigid support under protein-aptamer complex formation and washing conditions. As such, the poly(amino acids) can be non-covalently or covalently associated with the rigid support surface. Examples of non-covalent association include non-specific adsorption, specific binding through a specific binding pair member covalently attached to the support surface, and entrapment in a matrix material, e.g., a hydrated or dried separation medium. Examples of covalent binding include covalent bonds formed between the poly(amino acid) and a functional group present on the surface of the rigid support, e.g., OH, where the functional group may be naturally occurring or present as a member of an introduced linking group, as described in greater detail below.

By solid is meant that the support is rigid and does not readily bend, i.e. the support is not flexible. Examples of solid materials that are not rigid supports with respect to the present invention include membranes, flexible plastic films, and the like. As such, the solid support of the subject arrays and aptamers are sufficient to provide physical support and structure to the polymeric targets present thereon under the assay conditions in which the array is employed, particularly under high-throughput handling conditions.

The solid support upon which the subject patterns of poly(amino acids) are presented in the subject arrays or aptamers may take a variety of configurations, ranging from simple to complex, depending on the intended use of the array. Thus, the support could have an overall slide or plate configuration, such as a rectangular or disc configuration, where an overall rectangular configuration, as found in standard microplates and microscope slides, is preferred. Generally, the length of the rigid supports will be at least about 1 cm and may be as great as 40 cm or more, but will usually not exceed about 30 cm and may often not exceed about 15 cm. The width of the rigid support will generally be at least about 1 cm and may be as great as 30 cm, but will usually not exceed 20 cm and will often not exceed 10 cm. The height of the solid support will generally range from 0.01 mm to 10 mm, depending at least in part on the material from which the solid support is fabricated and the thickness of the material required to provide the requisite rigidity.

The solid support of the subject arrays or aptamers may be fabricated from a variety of materials. The materials from which the substrate is fabricated should ideally exhibit a low level of non-specific binding of specific binding pair members during protein-aptamer complex formation or specific binding events. In many situations, it will also be preferable to employ a material that is transparent to visible and/or UV light. Specific materials of interest include: glass; plastics, e.g., polytetrafluoroethylene, polypropylene, polystyrene, polycarbonate, and blends thereof, and the like; metals, e.g., gold, platinum, and the like; etc.

The solid support of the subject arrays or aptamers comprise at least one surface on which the array or aptamers are present, where the surface may be smooth or substantially planar, or have irregularities, such as depressions or elevations. The surface may be modified with one or more different layers of compounds that serve to modulate the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, poly(nucleic acids) or mimetics thereof, e.g., peptide nucleic acids and the like; polysaccharides, phospholipids, polyurethanes, polyesters, polycarbonates, polyureas, polyamides, polyethyleneimines, polyarylene sulfides, polysiloxanes, polyimides, polyacetates, and the like, where the polymers may be hetero- or homopolymeric, and may or may not have separate functional moieties attached thereto, e.g., conjugated.

Protein microarray production is a highly automated process, using either pin-based or microdispensing liquid handling robots to arrange biological samples on a flat surface for to generate high-density protein arrays and microarrays. This method involves using gridding robots that transfer either DNA or the corresponding protein expressed, from microplates on to poly(vinylidene difluoride) (Hybond-PVDF, Amersham) membranes in high-density grids. Protein microarrays can also be generated by spotting the purified protein from liquid expression cultures using a transfer stamp mounted onto a flat-bed spotting robot. In addition, there have been many other developments in this area, which have been recently reviewed. Such developments include the generation of low-density protein arrays on filter membranes, such as the universal protein array system (UPA). This is based on the 96-well microplate format. In this system, protein microarrays have been printed on an optically flat glass plate containing 96 wells formed by an enclosing hydrophobic Teflon mask. Inside the wells, arrays of 144 elements each, were spotted using a 36-capillary-based print head attached to a precise, high-speed, X-Y-Z robot. Standard ELISA techniques and a scanning CCD detector were used for imaging of arrayed antigens. Other approaches to protein microarrays that have been reported use either photolithography of silane or gold monolayers, combining microwells with microsphere sensors or ink-jetting onto polystyrene film. Such formats involve generating miniaturized immunoassay formats by patterning of single proteins (e.g., BSA, avidin or monoclonal antibodies). The current invention will aid in the quality control and detection of proteins immobilized on the various surfaces.

An optical response is detected qualitatively, or optionally quantitatively, by means that include visual inspection, CCD cameras, video cameras, photographic film, or the use of instrumentation such as laser scanning devices, fluorometers, photodiodes, quantum counters, epifluorescence microscopes, scanning microscopes, flow cytometers, fluorescence microplate readers, or by means for amplifying the signal such as photomultiplier tubes. Recording the optical response using POLAROID film results in enhanced sensitivity of signal. Responses to other detectable labels (radioactivity, electron spin, magnetic properties etc) is determined with instrumentation appropriate to the label.

Applications

The instant invention has useful applications in basic proteomic research applications, including but not limited to, 2-D gels in combination with Western blotting, aptamer technology, high-throughput screening, microarray technology, drug development, and medical diagnostics. The methods and kits of the invention can be used in a variety of assay formats for diagnostic applications in the disciplines of microbiology, immunology, hematology and blood transfusion. In general, the methods and kits of the current invention provide a versatile and convenient means to enhance the sensitivity and quantitative aspects of any assay that uses immobilized poly(amino acids) as part of its methodology.

The combination of Western blotting and high-resolution 2-D gel electrophoresis represents a rapid and simple method toward the identification of protein spots in complex mixtures, such as lysates from organs, tissues, cells, and body fluids. Frequently the 2-D gel electrophoresed proteins are transferred onto a solid support (blotting). These "blotted proteins" are analyzed for their antigenic properties (immunoblotting) using antibodies, though other protein-selective probes such as DNA, RNA, labeled aptamers, protein-binding ligands such as fluorescent penicillin analogs for penicillin-binding proteins and lectins can be used. To obtain a reference point in order to identity the protein of interest, a total protein pattern from the 2-D gel is required.

The instant invention can be used in conjunction with methods used to study poly(amino acids) as a diagnostic or prognostic using aptamers. Aptamers are DNA or RNA molecules that bind specific proteins. The specificity of aptamers allows them to distinguish between even closely related proteins, a key advantage for large-scale comprehensive diagnostics and for research proteomics. In addition to the superior specificity and affinity of aptamers, their advantages over current capture agent technologies include direct detection and cost efficiency. The use of aptamers allows screening of bodily fluids. For example, arrays of aptamers are bound to a solid support, and a sample is applied. The sample can be any biological sample including but not limited to blood or urine. Unbound protein is washed off, and the instant inventions is used to label that label proteins that are bound to the aptamer but not nucleic acids used to generate protein profiles. The instant invention can distinguish functional groups of amino acids from those of nucleic acids and will give a direct readout of proteins on the solid support, even in the presence of nucleic acids, which are essentially unreactive to the preferred amine-reactive dyes of this invention. Conversely, labeled aptamers can be used as protein-selective detection reagents for immobilized proteins.

The major advantages of using aptamers in high-throughput screening assays are speed of aptamer identification, high affinity of aptamers for protein targets, relatively large aptamer-protein interaction surfaces, and compatibility with various labeling/detection strategies. Aptamers may be particularly useful in high-throughput screening assays with protein targets that have no known binding partners such as orphan receptors. Since aptamers that bind to proteins are often specific and potent antagonists of protein function, the use of aptamers for target validation can be coupled with their subsequent use in high-throughput screening. Given the large size of many conventional and combinatorial libraries and the rapid increase in the number of possible therapeutic targets, the speed with which efficient high-throughput screening assays can be developed can be a rate-limiting step in the discovery process. Applications of the methods and kits of the current invention for detection of protein binding to immobilized aptamer arrays are expected to have the same advantages that they do for detection of proteins immobilized on blots since the same light sources are used in array readers as in commercially available blot readers.

Proteomics will also play an important role for drug discovery and development. Proteomics is the link between genes, proteins and disease. Many of the best-selling drugs either act by targeting proteins or are proteins. In addition, many molecular markers of disease, the basis of diagnostics, are proteins whose patterns of expression can be used as a guide to drug design. Application of proteomics to study underlying pharmaceutical mechanisms and to use this information for drug development is referred to as pharmaceutical proteomics. Unlike classical genomic approaches that discover genes related to a disease, proteomics could characterize the disease process directly by finding sets of proteins (pathways or clusters) that participate together in causing the disease. The same technology is used to study the effects of candidate drugs intended to reverse a disease process.

EXAMPLES

The following examples describe specific aspects of the invention to illustrate the invention and to provide a description of the methods for those of skill in the art. The examples should not be construed as limiting the invention, as the examples merely provide specific methodology useful in understanding and practicing the invention. The reagents employed in the examples are commercially available or can be prepared using commercially available instrumentation, methods, or reagents known in the art. The foregoing examples illustrate various aspects of the invention and practice of the methods of the invention. Each of the references cited in the examples is incorporated herein by reference in its entirety. The examples are not intended to provide an exhaustive description of the many different embodiments of the invention nor to limit the selection of suitable dyes beyond what has already been described above. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

1. Simultaneous Dichromatic Detection of Total Protein and a Specific Target Protein Using BODIPY FL-X Succinimidyl Ester and DDAO Phosphate.

A mixture of a dilution series of tubulin (500 ng/lane—0.244 ng/lane) and a constant 250 ng/lane broad range markers (including myosin, β-galactosidase, phosphorylase b, serum albumin, ovalbumin, carbonic anhydrase, trypsin inhibitor, lysozyme and aprotinin) were separated by SDS-polyacrylamide gel electrophoresis utilizing a 4% T, 2.6% C stacking gel, pH 6.8 and a 13% T, 2.6% C separating gel, pH 8.8 according to standard procedures. % T is the total monomer concentration (acrylamide+crosslinker) expressed in grams per 100 mL and % C is the percentage crosslinker (e.g., N,N'-methylene-bis-acrylamide, N,N'-diacryloylpiperazine or other suitable agent). After electrophoresis, proteins were transferred to a poly(vinylidene difluoride) (PVDF) membrane by electroblotting. The membranes were allowed to dry to minimize loss of proteins during subsequent manipulations. Membranes were equilibrated by incubation for 10 minutes (two times) in 10 mM sodium borate buffer, pH 9.5. After equilibration, the membranes were stained for 30 minutes with 10 μM BODIPY FL-X, succinimidyl ester in the same buffer. After two 5–10 minute washes in 100% methanol, the membranes were rinsed with $dH_2O$ and allowed to air dry. Immunodetection was performed by standard procedures, including a 1 hour blocking step, 2 hour primary antibody incubation, and 1 hour alkaline phosphatase-conjugated secondary antibody incubation at room temperature with agitation. The blocking buffer contained 0.25% MOWIOL 4–88, 0.5% BSA and 0.2% Tween 20. To detect the presence of the alkaline phosphatase-conjugated secondary antibody on the blot, the membranes were incubated for 30 minutes with 1.25 μg/mL DDAO phosphate in a buffer containing 1 mM $MgCl_2$ and 10 mM Tris, pH 9.5. Proteins were viewed using a 300 nm UV epi-illuminator. The total protein profile appeared green fluorescent while the specific target was stained red fluorescent. Membranes can also be imaged using a laser system such as the Fuji FLA-3000 imager utilizing the 633 nm excitation filter and 675 nm emission filter for the DDAO dye and a 473 nm excitation filter and 520 nm emission filter for the BODIPY FL-X dye. Other BODIPY dyes can be utilized similarly.

2. Serial Dichromatic Detection of a Specific Target Using DDAO Phosphate Followed by Total Protein Detection Using BODIPY FL-X Succinimidyl Ester.

Proteins were separated by SDS-polyacrylamide gel electrophoresis and electroblotted by standard methods. The membranes were allowed to dry to minimize loss of proteins during subsequent manipulations. Immunodetection was performed by standard procedures. To detect the presence of the alkaline phosphatase-conjugated secondary antibody on the blot the membranes were incubated for 30 minutes with 1.25 μg/mL DDAO phosphate in a buffer containing 1 mM $MgCl_2$ and 10 mM Tris, pH 9.5. Viewing membranes by UV illumination or using a 633 nm helium-neon laser scanner revealed a red-fluorescent signal associated with the target protein. The membranes were allowed to dry and were then equilibrated by incubation for 10 minutes (two times) in 10 mM sodium borate buffer, pH 9.5. After equilibration, the membranes were stained for 30 minutes with 10 μM BODIPY FL-X, succinimidyl ester in the same buffer. After 5–10 minute washes in 100% methanol the membranes were rinsed with $dH_2O$ and allowed to dry. Proteins were viewed using a 300 nm UV epi-illuminator. The total protein profile appeared green fluorescent while the specific target was not detected because the DDAO dye does not precipitate on the membrane and was washed off during subsequent staining steps. Other BODIPY dyes can be utilized similarly.

3. Stripping Dichromatic Membranes of the DDAO Signal to Allow Re-Probing with Another Antibody.

Proteins were separated by SDS-polyacrylamide gel electrophoresis and subsequently electroblotted by standard methods, as described in the previous examples. The membranes were allowed to dry to minimize loss of proteins during subsequent manipulations. Membranes were equilibrated by incubation for 10 minutes (two times) in 10 mM sodium borate buffer, pH 9.5. After equilibration, the membranes were stained for 30 minutes with 10 μM BODIPY FL-X, SE in the same buffer. After 5–10 minute washes in 100% methanol, the membranes were rinsed with dH$_2$O and allowed to dry. Immunodetection was performed by standard methods, as described in the previous examples. To detect the presence of the alkaline phosphatase-conjugated secondary antibody on the blot the membranes were incubated for 30 minutes with 1.25 μg/nL DDAO phosphate (Molecular Probes, Inc, Eugene, Oreg.) in a buffer containing 1 mM MgCl$_2$ and 10 mM Tris, pH 9.5. Proteins were viewed using a 300 nm UV epi-illuminator. The total protein profile appeared green fluorescent while the specific target was stained red fluorescent. After initial verification of protein labeling, the membranes were stripped by incubating them for 1 hour, at 500, in buffer containing 2% SDS, 62.5 mM Tris-HCl, pH 6.8 and 50 mM DTT. After rinsing the membranes with 50 mM Tris, pH 7.5 and 150 mM NaCl, proteins previously detected with the DDAO dye were no longer visible using a 300 nm UV epi-illuminator. The total protein profile still appeared green fluorescent. These membranes could be incubated with another monoclonal antibody and an alkaline phosphatase- or horseradish peroxidase-conjugated secondary antibody in combination with suitable enzyme substrates, permitting detection of a different antigen on the blot. The green-fluorescent BODIPY FL dye signal remained, even after the stripping and re-probing steps. Other BODIPY dyes can be utilized similarly.

4. Simultaneous Dichromatic Detection of Total Protein and a Specific Target Protein Using BODIPY TR-X Succinimidyl Ester and ELF 97 Phosphate.

Proteins were separated by SDS-polyacrylamide gel electrophoresis and electroblotted by standard methods, as described in Example 1. The membranes were allowed to dry to minimize loss of proteins during subsequent manipulations. Membranes were equilibrated by incubation for 10 minutes (two times) in 10 mM sodium borate buffer, pH 9.5. After equilibration, the membranes were stained for 30 minutes with 10 μM BODIPY TR-X, SE in the same buffer. After two 5–10 minute washes in 100% methanol the membranes were rinsed with dH$_2$O and allowed to dry. Immunodetection was performed by standard procedures. To detect the presence of the alkaline phosphatase-conjugated secondary antibody on the blot the membranes were incubated for 30 minutes with 10 μg/nL ELF 97 phosphate in a buffer containing 1 mM MgCl$_2$ and 10 mM Tris, pH 9.5. Proteins were viewed using 300 nm UV epi-illumination. The total protein profile appeared red fluorescent while the specific target was stained green fluorescent. Labeling with the ELF 97 phosphate substrate prior to labeling with BODIPY TR-X succinimidyl ester produced the same results. Other BODIPY dyes can be utilized similarly.

5. Dichromatic Detection Using BODIPY TR-X Succinimidyl Ester and ELF 97 Phosphate Followed by Stripping of the Membranes for Re-Probing.

Proteins were separated by SDS-polyacrylamide gel electrophoresis and electroblotted, as described in Example 1. The membranes were allowed to dry to minimize loss of proteins during subsequent manipulations. Membranes were equilibrated by incubation for 10 minutes (two times) in 10 mM sodium borate buffer, pH 9.5. After equilibration, the membranes were stained for 30 minutes with 10 μM BODIPY TR-X, SE in the same buffer. After 5–10 minute washes in 100% methanol the membranes were rinsed with dH$_2$O and allowed to dry. Immunodetection was performed by standard procedures. To detect the presence of the alkaline phosphatase-conjugated secondary antibody on the blot the membranes were incubated for 30 minutes with 10 μg/mL ELF 97 phosphate in a buffer containing 1 mM MgCl$_2$ and 10 mM Tris, pH 9.5. Proteins were viewed using 300 nm UV epi-illumination. The total protein profile appeared red fluorescent while the specific target was stained green fluorescent. After initial verification of protein labeling, the membranes were incubated for 1 hour, at 50° C., in buffer containing 2% SDS, 62.5 mM Tris-HCl, pH 6.8 and 50 mM DTT. After rinsing the membranes with 50 mM Tris, pH 7.5, 150 mM NaCl, proteins previously detected with ELF 97 phosphate were still visible using a 300 nm UV epi-illuminator. This demonstrates that the ELF 97 alcohol precipitate was permanent. The total protein profile appeared as red-fluorescent bands. Other BODIPY dyes can be utilized similarly.

6. Simultaneous Dichromatic Detection of a Specific Target Using BCIP/NBT Followed by Total Protein Detection Using BODIPY TR-X Succinimidyl Ester.

Proteins were separated by SDS-polyacrylamide gel electrophoresis and electroblotted as described in Example 1. The membranes were allowed to dry to minimize loss of proteins during subsequent manipulations. Immunodetection was performed by standard procedures. To detect the presence of the alkaline phosphatase-conjugated secondary antibody on the blot the membranes were incubated for 3–60 minutes in NBT/BCIP in a buffer containing 100 mM Tris, pH 9.5, 50 mM MgCl$_2$ and 100 mM NaCl. The endpoint of incubation was determined by eye, based upon color development. The membranes were allowed to dry and were then equilibrated by incubation for 10 minutes (two times) in 10 mM sodium borate buffer, pH 9.5. After equilibration, the membranes were stained for 30 minutes with 10 μM BODIPY TR-X, succinimidyl ester in the same buffer. After two 5–10 minute washes in 100% methanol the membranes were rinsed with dH$_2$O and allowed to dry. The total protein profile was viewed using 300 nm UV epi-illumination and appeared red fluorescent while the NBT/BCIP signal associated with the specific target appeared blue colored when using white light to visualize the signal. NBT/BCIP was normally purple in color but when followed by BODIPY TR-X, succinimidyl ester it appeared blue. Other BODIPY dyes can be utilized similarly.

7. Serial Dichromatic Detection of Total Protein Using BODIPY TR-X Succinimidyl Ester Followed by a Specific Target Using NBT/BCIP.

Proteins were separated by SDS-polyacrylamide gel electrophoresis and electroblotted, as described in Example 1. The membranes were allowed to dry to minimize loss of proteins during subsequent manipulations. Membranes were then equilibrated by incubation for 10 minutes (two times) in 10 mM sodium borate buffer, pH 9.5. After equilibration, the membranes were stained for 30 minutes with 10 μM BODIPY TR-X, succinimidyl ester in the same buffer. After two 5–10 minute washes in 100% methanol the membranes were rinsed with dH$_2$O and allowed to dry. Proteins appeared as red-fluorescent bands when visualized by UV epi-illumination. Immunodetection was performed by standard procedures. To detect the presence of the alkaline phosphatase-conjugated secondary antibody on the blot the membranes were incubated for 3–60 minutes in NBT/BCIP in a buffer containing 100 mM Tris, pH 9.5, 50 mM MgCl$_2$, and 100 mM NaCl. The endpoint of incubation was determined by eye based on color development. The red fluorescence of the BODIPY dye was quenched by the NBT/BCIP. The NBT/BCIP precipitate appears purple by eye. Other BODIPY dyes can be utilized similarly.

8. Simultaneous Dichromatic Detection of Total Protein and a Specific Target Using BODIPY TR-X Succinimidyl Ester and Fluoroblot™ Peroxidase Substrate.

Proteins were separated by SDS-polyacrylamide gel electrophoresis and electroblotted, as described in Example 1. The membranes were then allowed to dry to minimize loss of proteins during subsequent manipulations. Membranes were then equilibrated by incubation for 10 minutes (two times) in 10 mM sodium borate buffer, pH 9.5. After equilibration, the membranes were stained for 30 minutes with 10 $\mu$M BODIPY TR-X, SE in the same buffer. After 5–10 minute washes in 100% methanol the membranes were rinsed with $dH_2O$ and allowed to dry. Immunoblotting was performed by standard procedures including a 1 hour blocking step, 2 hour primary antibody incubation, and 1 hour horseradish peroxidase-conjugated secondary antibody incubation at room temperature with agitation. The blocker included 0.25% MOWIOL 4–88, 0.5% BSA, and 0.2% Tween 20. To detect the presence of the horseradish peroxidase-conjugated secondary antibody on the blot the membranes were incubated for 30 minutes in Fluoroblot peroxidase substrate (Pierce Chemical Company, Milwaukee, Wis.) diluted 1:1 in stable peroxidase buffer. Proteins were viewed using 300 nm UV epi-illumination. The total protein profile appeared red fluorescent while the specific target was stained green fluorescent. The Fluoroblot dye-labeled proteins were viewed best when the membranes were wet because the fluorescence was considerably reduced upon drying. Other BODIPY dyes can be utilized similarly.

9. Serial Dichromatic Detection of a Specific Target Followed by Total Protein Detection Using Fluoroblot Peroxidase Substrate and BODIPY Dyes.

Proteins were separated by SDS-polyacrylamide gel electrophoresis and electroblotted, as described in Example 1. The membranes were then allowed to dry to minimize loss of proteins during subsequent manipulations. Immunodetection was performed by standard procedures. To detect the presence of the horseradish peroxidase-conjugated secondary antibody on the blot the membranes were incubated for 30 minutes in Fluoroblot peroxidase substrate diluted 1:1 in stable peroxidase buffer. Upon viewing with a 300 nm epi-illumination source, the target protein appeared green fluorescent. The membranes were allowed to dry and were then equilibrated by incubation for 10 minutes (two times) in 10 mM sodium borate buffer, pH 9.5. After equilibration, the membranes were stained for 30 minutes with 10 $\mu$M BODIPY TR-X, succinimidyl ester in the same buffer. After 5–10 minute washes in 100% methanol the membranes were rinsed with $dH_2O$ and allowed to dry. Proteins were viewed using 300 nm UV epi-illumination. The total protein profile appeared fluorescent red while the specific target was no longer detected because the Fluoroblot dye was washed off the membrane in the subsequent BODIPY dye staining steps. Other BODIPY dyes can be utilized similarly.

10. Simultaneous Dichromatic Detection of Total Protein and a Specific Target Using BODIPY TR-X Succinimidyl Ester and Amplex Gold Substrate.

Proteins were separated by SDS-polyacrylamide gel electrophoresis and electroblotted, as described in Example 1. The membranes were then allowed to dry to minimize loss of proteins during subsequent manipulations. Membranes were then equilibrated by incubation for 10 minutes (two times) in 10 mM sodium borate buffer, pH 9.5. After equilibration, the membranes were stained for 30 minutes with 10 $\mu$M BODIPY TR-X, SE in the same buffer. After 5–10 minute washes in 100% methanol the membranes were rinsed with $dH_2O$ and allowed to dry. Immunoblotting was performed by standard procedures including a 1 hour blocking step, 2 hour primary antibody incubation, and 1 hour horseradish peroxidase-conjugated secondary antibody incubation at room temperature with agitation. The blocker included 0.25% MOWIOL 4–88, 0.5% BSA, and 0.2% Tween 20. To detect the presence of the horseradish peroxidase-conjugated secondary antibody on the blot the membranes were incubated for 30 minutes with 50 $\mu$M Amplex Gold in a buffer containing 1 mM $MgCl_2$, 280 $\mu$M $ZnCl_2$, 10 mM Tris, pH 9.5 and 200 $\mu$M $H_2O_2$. Proteins were viewed using a 300 nm UV epi-illuminator. The total protein profile appeared red fluorescent while the specific target was labeled goldenrod. Proteins were viewed using a 300 nm UV epi-illuminator. Membranes could also have been imaged using a laser system such as the Fuji FLA-3000 imager utilizing the 633 nm excitation filter and 675 nm emission filter for the BODIPY TR-X dye and a 532 nm excitation filter and 580 nm emission filter for Amplex Gold. Other BODIPY dyes can be utilized similarly.

11. Serial Dichromatic Detection of Total Protein and a Specific Target Using BODIPY TR-X Succinimidyl Ester and 4-chloro-1-naphthol.

Proteins were separated by SDS-polyacrylamide gel electrophoresis and electroblotted, as described in Example 1. The membranes were allowed to dry to minimize loss of proteins during subsequent manipulations. Membranes were then equilibrated by incubation for 10 minutes (two times) in 10 mM sodium borate buffer, pH 9.5. After equilibration, the membranes were stained for 30 minutes with 10 $\mu$M BODIPY TR-X, SE in the same buffer. After two 5–10 minute washes in 100% methanol the membranes were rinsed with $dH_2O$ and allowed to dry. Proteins appeared as red-fluorescent bands upon 300 nm UV epi-illumination. Immunodetection was performed by standard procedures. To detect the presence of the horseradish peroxidase-conjugated secondary antibody on the blot the membranes were incubated for 3–60 minutes in 4-chloro-1-naphthol solution (0.48 mM 4-chloro-1-naphthol, 50 mM Tris HCl, 0.2 mM NaCl and 17% methanol) to which was added 0.01% (v/v) hydrogen peroxide. The endpoint of incubation was determined by eye based upon color development. The fluorescence of the total protein profile was quenched by the 4-chloro-1-naphthol. The 4-chloro-1-naphthol labeling of the specific target protein appears purple by eye when viewed using white-light illumination. Other BODIPY dyes can be utilized similarly.

12. Simultaneous Dichromatic Detection of a Specific Target Using 4-chloro-1-naphthol Followed by Total Protein Staining Using BODIPY TR-X Succinimidyl Ester.

Proteins were separated by SDS-polyacrylamide gel electrophoresis and electroblotted as described in Example 1. The membranes were allowed to dry to minimize loss of proteins during subsequent manipulations. Immunodetection was performed by standard procedures. To detect the presence of the horseradish peroxidase-conjugated secondary antibody on the blot the membranes were incubated for 3–60 minutes in 4-chloro-1-naphthol solution (0.48 mM 4-chloro-1-naphthol, 50 mM Tris HCl, 0.2 mM NaCl and 17% methanol) to which 0.01% (v/v) hydrogen peroxide was added. The membranes were allowed to dry and were then equilibrated by incubation for 10 minutes (two times) in 10 mM sodium borate buffer, pH 9.5. After equilibration, the membranes were stained for 30 minutes with 10 $\mu$M BODIPY TR-X, SE in the same buffer. After two 5–10 minute washes in 100% methanol the membranes were rinsed with dH$_2$O and allowed to dry. Proteins were viewed using 300 nm UV epi-illumination. The total protein profile appeared red fluorescent. The specific target appears purple when viewed by white-light illumination. Other BODIPY dyes can be utilized similarly.

13. Serial Dichromatic Detection of Total Protein and a Specific Target Using BODIPY TR-X Succinimidyl Ester and 3,3'-diaminobenzidine Tetrahydrochloride.

Proteins were separated by SDS-polyacrylamide gel electrophoresis and electroblotted as described in Example 1. The membranes were then allowed to dry to minimize loss of proteins during subsequent manipulations. Membranes were then equilibrated by incubation for 10 minutes (two times) in 10 mM sodium borate buffer, pH 9.5. After equilibration, the membranes were stained for 30 minutes with 10 μM BODIPY TR-X, succinimidyl ester in the same buffer. After 5–10 minute washes in 100% methanol the membranes were rinsed with dH$_2$O and allowed to dry. Upon viewing with a 300 nm UV epi-illumination source, proteins appeared as red-fluorescent bands. Immunodetection was performed by standard procedures. To detect the presence of the horseradish peroxidase-conjugated secondary antibody on the blot the membranes were incubated for 3–60 minutes with 0.6 mg/mL 3,3'-diaminobenzidine in 50 mM Tris, pH 7.6, 0.03% hydrogen peroxide (v/v). The endpoint of incubation was determined by eye based upon color development. The fluorescence of the total protein profile was quenched by the 3,3'-diaminobenzidine. The 3,3'-diaminobenzidine labeling the specific target protein appeared brown on the blot when viewed by white-light illumination. Other BODIPY dyes can be utilized similarly.

14. Simultaneous Dichromatic Detection of Total Protein and a Specific Target Using BODIPY TR-X Succinimidyl Ester and 3,3'-diaminobenzidine.

Proteins were separated by SDS-polyacrylamide gel electrophoresis and electroblotted as described in Example 1. The membranes were then allowed to dry to minimize loss of proteins during subsequent manipulations. Immunoblotting was performed by standard procedures. To detect the presence of the horseradish peroxidase-conjugated secondary antibody on the blot the membranes were incubated for 3–60 minutes with 0.6 mg/mL 3,3'-diaminobenzidine in 50 mM Tris, pH 7.6, 0.03% hydrogen peroxide (v/v). The membranes were allowed to dry and were then equilibrated by incubation for 10 minutes (two times) in 10 mM sodium borate buffer, pH 9.5. After equilibration, the membranes were stained for 30 minutes with 10 μM BODIPY TR-X, SE in the same buffer. After 5–10 minute washes in 100% methanol, the membranes were rinsed with dH$_2$O and allowed to dry. Proteins were viewed as red-fluorescent bands using 300 nm UV epi-illumination. The specific target was labeled brown and was easily viewed using white-light illumination. Other BODIPY dyes can be utilized similarly.

15. Simultaneous Dichromatic Detection of a Specific Target Using Alexa Fluor 488 Tyramide Conjugate and Total Protein Using BODIPY TR-X Succinimidyl Ester.

Proteins were separated by SDS-polyacrylamide gel electrophoresis and electroblotted as described in Example 1. The membranes were then allowed to dry to minimize loss of proteins during subsequent manipulations. Immunodetection was performed by standard procedures. To detect the presence of the horseradish peroxidase-conjugated secondary antibody on the blot the membranes were incubated for 30 minutes in 5 μM Alexa Fluor 488 tyramide (Molecular Probes, Inc, Eugene Oreg., U.S. Pat. No. 6,130,101 and U.S. patent Ser. No. 09/969,853, incorporated by reference) in 50 mM Tris, pH 7.5 and 150 mM NaCl to which was added 0.03% hydrogen peroxide (v/v). The membranes were allowed to dry and were then equilibrated by incubation for 10 minutes (two times) in 10 mM sodium borate buffer, pH 9.5. After equilibration, the membranes were stained for 30 minutes with 10 μM BODIPY TR-X, SE in the same buffer. After 5–10 minute washes in 100% methanol the membranes were rinsed with dH$_2$O and allowed to dry. Proteins can be viewed using 300 nm UV epi-illumination. The total protein profile appeared red fluorescent while the specific target appeared green fluorescent. Other BODIPY dyes can be utilized similarly in combination with appropriately selected fluorescent tyramide derivatives.

16. Simultaneous Dichromatic Detection of Glycoproteins and Total Proteins Using BODIPY TR-X Succinimidyl Ester and PRO-Q EMERALD 300 Glycoprotein Stain on Membranes.

Proteins were separated by SDS-polyacrylamide gel electrophoresis and electroblotted, as described in Example 1. The membranes were then allowed to dry to minimize loss of proteins during subsequent manipulations. The membranes were then equilibrated by incubation for 10 minutes (two times) in 10 mM sodium borate buffer, pH 9.5. After equilibration, the membranes were stained for 30 minutes with 10 μM BODIPY TR-X, SE in the same buffer. After 5–10 minute washes in 100% methanol the membranes were rinsed with dH$_2$O and allowed to dry. The membranes were then fixed in 50% methanol, oxidized in 1% periodic acid in 3% acetic acid and stained with 5 μM PRO-Q EMERALD 300 in 2% DMF, 250 mM MgCl$_2$, and 3% acetic acid. After staining, the membranes were rinsed in 3% acetic acid followed by dH$_2$O and allowed to dry. Proteins were viewed using 300 nm UV epi-illumination. The total protein profile appeared red fluorescent while the glycoproteins were green fluorescent. Labeling with the PRO-Q EMERALD 300 dye prior to labeling with BODIPY TR-X succinimidyl ester produced the same results. Other BODIPY dyes can be utilized similarly.

17. Simultaneous Dichromatic Detection of Glycoproteins and Total Proteins Using BODIPY TR-X Succinimidyl Ester and PRO-Q EMERALD 300 Glycoprotein Stain in Gels.

Proteins were separated by SDS-polyacrylamide gel electrophoresis, as described in Example 1. After electrophoresis, gels were fixed overnight in MeOH: acetic acid: H$_2$O (5:1:1). They were then washed and equilibrated in 10 mM sodium borate buffer, pH 9.5, and stained in 10 μM BODIPY TR-X, SE in the same buffer. After washing, the gels were fixed in 50% methanol, oxidized in 1% periodic acid in 3% acetic acid and stained with 5 μM PRO-Q EMERALD 300 in 2% DMF, 250 mM MgCl$_2$, and 3% acetic acid. After staining, the gels were rinsed in 3% acetic acid followed by dH$_2$O. Proteins stained with PRO-Q EMERALD 300 can be viewed using an imaging system such as the Roche Lumi-Imager, which utilizes a UV light box and a CCD camera. PRO-Q EMERALD 300 dye-stained proteins can be visualized using the 520 nm+/−20 emission filter. BODIPY TR-X dye-conjugated proteins were visualized and separated from PRO-Q EMERALD 300 dye-stained proteins using the 590/10 excitation filter and a 625/30 emission filter.

18. Simultaneous Dichromatic Detection of Glycoproteins Using Lectin Concanavalin A, Alkaline Phosphatase Conjugate and BODIPY TR-X Succinimidyl Ester.

Proteins were separated by SDS-polyacrylamide gel electrophoresis and electroblotted, as described in Example 1.

The membranes were then allowed to dry to minimize loss of proteins during subsequent manipulations. The membranes were then equilibrated by incubation for 10 minutes (two times) in 10 mM sodium borate buffer, pH 9.5. After equilibration, the membranes were stained for 30 minutes with 10 µM BODIPY TR-X, SE in the same buffer. After two 5–10 minute washes in 100% methanol the membranes were rinsed with dH$_2$O and allowed to dry. For detection of the glycoproteins described above, the membranes were blocked then incubated in 1 µg/mL concanavalin A-alkaline phosphatase in a buffer containing 150 mM mTBS, 50 Tris, pH 7.5, 0.2% Tween-207, 0.25% Mowiol 4–88, 0.5 mM MgCl$_2$, and 1 mM CaCl$_2$. For detection of the concanavalin A-AP conjugate, the membranes were incubated with 10 µg/mL ELF 97 phosphate in a buffer containing 1 mM MgCl$_2$ and 10 mM Tris, pH 9.5. Proteins were viewed using 300 nm UV epi-illumination. Concanavalin A binds to glycoproteins containing α-mannosyl and α-glucopyranosyl residues. The total protein profile appeared red fluorescent while the targeted glycoproteins were stained green fluorescent.

19. Simultaneous Dichromatic Detection of Glycoproteins Using Lectin Concanavalin A, Alkaline Phosphatase Conjugate and BODIPY FL-X Succinimidyl Ester.

Proteins were separated by SDS-polyacrylamide gel electrophoresis and electroblotted as described in Example 1. The membranes were then allowed to dry to minimize loss of proteins during subsequent manipulations. The membranes were then equilibrated by incubation for 10 minutes (two times) in 10 mM sodium borate buffer, pH 9.5. After equilibration, the membranes were stained for 30 minutes in 10 µM BODIPY FL-X, SE in the same buffer. After two 5–10 minute washes in 100% methanol the membranes were rinsed with dH$_2$O and allowed to dry. For detection of the glycoproteins described above, the membranes were blocked then incubated in 1 µg/mL concanavalin A-alkaline phosphatase in a buffer containing 150 mM mTBS, 50 Tris, pH 7.5, 0.2% Tween-20, 0.25% Mowiol 4–88, 0.5 mM MgCl$_2$ and 1 mM CaCl$_2$. For detection of the concanavalin A-AP conjugate, the membranes were incubated in 1.25 µg/mL DDAO phosphate in a buffer containing 1 mM MgCl$_2$ and 10 mM Tris, pH 9.5. Proteins were viewed using a 300 nm UV epi-illuminator. The total protein profile appeared green fluorescent while the targeted glycoproteins were stained red fluorescent. Membranes can also be imaged using a laser system such as the Fuji FLA-3000 imager utilizing the 633 nm excitation filter and 675 nm emission filter for the DDAO dye and a 473 nm excitation filter and 520 nm emission filter for the BODIPY FL-X dye.

20. Simultaneous Dichromatic Detection of Glycoproteins Using Lectin Wheat Germ Agglutinin and BODIPY TR-X Succinimidyl Ester.

Proteins were separated by SDS-polyacrylamide gel electrophoresis and electroblotted, as described in Example 1. The membranes were then allowed to dry to minimize loss of proteins during subsequent manipulations. The membranes were then equilibrated by incubation for 10 minutes (two times) in 10 mM sodium borate buffer, pH 9.5. After equilibration, the membranes were stained for 30 minutes with 10 µM BODIPY TR-X, SE in the same buffer. After two 5–10 mL washes in 100% methanol the membranes were rinsed with dH$_2$O and allowed to dry. For detection of the glycoproteins described above, the membranes were blocked then incubated with 0.5 µg/mL wheat germ agglutinin-alkaline phosphatase in a buffer containing 150 mM mTBS, 50 Tris, pH 7.5, 0.2% Tween-20, 0.25% Mowiol 4–88, 0.5 mM MgCl$_2$, and 1 mM CaCl$_2$. For detection of the wheat germ agglutinin-AP conjugate, the membranes were incubated with 10 µg/mL ELF 97 phosphate in a buffer containing 1 mM MgCl$_2$ and 10 mM Tris, pH 9.5. Proteins were viewed using 300 nm UV epi-illumination. Wheat germ agglutinin binds glycoproteins containing N-acetylglucosamine and N-acetylneuraminic acid residues. The total protein profile appeared red fluorescent while the targeted glycoproteins were stained green fluorescent.

21. Simultaneous Dichromatic Detection of Glycoproteins Using Lectin Wheat Germ Agglutinin and BODIPY FL-X Succinimidyl Ester.

Proteins were separated by SDS-polyacrylamide gel electrophoresis and electroblotted, as described in Example 1. The membranes were then allowed to dry to minimize loss of proteins during subsequent manipulations. The membranes were then equilibrated by incubation for 10 minutes (two times) in 10 mM sodium borate buffer, pH 9.5. After equilibration, the membranes were stained for 30 minutes with 10 µM BODIPY FL-X, SE in the same buffer. After two 5–10 minute washes in 100% methanol the membranes were rinsed with dH$_2$O and allowed to dry. For detection of the glycoproteins described above, the membranes were blocked then incubated with 0.5 µg/mL wheat germ agglutinin-alkaline phosphatase in a buffer containing 150 mM mTBS, 50 Tris, pH 7.5, 0.2% Tween-20, 0.25% Mowiol 4–88, 0.5 mM MgCl$_2$, and 1 mM CaCl$_2$. For detection of the wheat germ agglutinin-AP conjugate, the membranes were incubated with 1.25 µg/ml DDAO phosphate in a buffer containing 1 mM MgCl$_2$ and 10 mM Tris, pH 9.5. Proteins can be viewed using a 300 nm UV epi-illuminator. The total protein profile appeared green fluorescent while the glycoproteins were stained red fluorescent. Membranes can also be imaged using a laser system such as the Fuji FLA-3000 imager utilizing the 633 nm excitation filter and 675 nm emission filter for the DDAO dye and a 473 nm excitation filter and 520 nm emission filter for the BODIPY FL-X dye.

22. Simultaneous Dichromatic Detection of Total Protein and a Specific Target Protein Using BODIPY FL-X Succinimidyl Ester in 2-D Electrophoresis and DDAO Phosphate.

150 µg of a rat fibroblast lysate was applied to 1 mm diameter, 20 cm long isoelectric focusing gels consisting of a 4% T, 2.6% C polyacrylamide gel matrix, containing 9 M urea, 2% Triton X-100, and 2% carrier ampholytes. Gels were run vertically for 18,000 volt-hours using 10 mM phosphoric acid and 100 mM sodium hydroxide as the anode and cathode buffer, respectively. Isoelectric focusing gels were incubated in 0.3 M Tris base, 0.075 M Tris-HCl, 3% SDS, 0.01% bromophenol blue for two minutes. Isoelectric focusing gels were then laid on top of 1 mm thick, 20 cm×20 cm, 12.5% T, 2.6% C polyacrylamide gels containing 375 mM Tris-base, pH 8.8 and SDS-polyacrylamide gel electrophoresis was performed according to standard procedures except that the cathode electrode buffer was 50 mM Tris, 384 mM glycine, 4% sodium dodecyl sulfate, pH 8.8 while the anode electrode buffer is 25 mM Tris, 192 mM glycine, 2% sodium dodecyl sulfate, pH 8.8. After the second dimension electrophoresis, proteins were transferred to a 20 cm×20 cm piece of poly(vinylidene difluoride) (PVDF) membrane by electroblotting. The membranes were allowed to dry to minimize loss of proteins during subsequent manipulations. Membranes were equilibrated by incubation for 10 minutes (two times) in 10 mM sodium borate buffer, pH 9.5. After equilibration, the membranes were stained for 30 minutes with 10 µM BODIPY FL-X, succinimidyl ester in the same buffer. After two 5–10 minute washes in 100% methanol, the membranes were rinsed with dH$_2$O and allowed to air dry. Immunodetection was performed by standard procedures, including a 1 hour blocking step, 2 hour primary antibody incubation, and 1 hour alkaline phosphatase-conjugated secondary antibody incubation at room temperature with agitation. The blocking buffer contained 0.25% Mowiol 4–88, 0.5% BSA and 0.2% Tween 20. To detect the presence of the alkaline phosphatase-conjugated secondary antibody on the membrane, the membranes were incubated for 30 minutes with 1.25 µg/mL DDAO phosphate in a buffer that contained 1 mM MgCl$_2$ and 10 mM Tris, pH 9.5. Proteins were viewed using a 300 nm UV epi-illuminator. The total protein profile appeared green fluorescent while the specific target was stained red fluorescent. Membranes can also be imaged using a laser system such as the Fuji FLA-3000 imager utilizing the 633 nm excitation filter and 675 nm emission filter for the DDAO dye and a 473 nm excitation filter and 520 nm emission filter for the BODIPY FL-X dye. Other BODIPY dyes can be utilized similarly.

23. Trichromatic Detection of Two Specific Targets Using ELF 39 Phosphate, Alexa Fluor 350 and BODIPY TR-X Succinimidyl Ester in 2-D Electrophoresis.

300 µg of bovine heart mitochondria were diluted to 5 mg/mL into 25 mM Tris, 2 mM EDTA, pH 7.5. Just prior to extraction, 1 mM PMSF was added, followed by 1% n-dodecyl-β-D-maltoside for the actual extraction. The mitochondria were incubated in the detergent for 20 minutes before the insoluble material was pelleted by centrifugation (10 min, 12,000 rpm). The protein in the supernatant was precipitated with 10% TCA and pelleted by centrifugation. The pellet was resuspended in urea sample buffer (7 M urea, 2 M thiourea, 1% Zwittergent 3–10, 2% CHAPS, 0.8% carrier Ampholytes) and frozen at –20° C. IPG strips (3–10 NL) were rehydrated overnight at room temperature in the same urea buffer (450 mL). The IPG strip was placed into the pHaser isoelectric focusing system and the sample was applied on a piece of filter paper at the anodic end. The sample was subjected to isolelectric focusing at 20° C. for 24.5 h (70,000 Vh) and then separated on a 20 cm×20 cm×1 mm second dimension SDS-polyacrylamide gel (12.5% T, 2.6% C). After second dimension electrophoresis, proteins were transferred to a 20 cm×20 cm piece of PVDF membrane by electroblotting. The membranes were allowed to dry to minimize loss of proteins during subsequent manipulations. Membranes are equilibrated by incubation for 10 minutes (two times) in 10 mM sodium borate buffer, pH 9.5. After equilibration, the membranes were stained for 30 minutes with 10 µM BODIPY TR-X, succinimidyl ester in the same buffer. After two 5–10 minute washes in 100% methanol, the membranes were rinsed with dH$_2$O and allowed to air dry. Immunodetection was performed by standard procedures except that two primary antibodies to two different targets were applied to the membrane. One primary antibody was directly conjugated to the Alexa Fluor 350 dye and the other was a mouse monoclonal antibody that was subsequently detected with a goat anti-mouse-alkaline phosphatase secondary antibody. To detect the presence of the alkaline phosphatase-conjugated secondary antibody on the blot, the membranes were incubated for 30 minutes in 10 µg/mL ELF 97 phosphate in a buffer containing 1 mM MgCl$_2$ and 10 mM Tris, pH 9.5. Proteins were viewed using 300 nm UV epi-illumination. The total protein profile appeared red fluorescent while one specific target was stained green fluorescent and the other was labeled blue fluorescent.

24. Trichromatic Detection of Two Specific Targets Using ELF 97 Phosphate, Streptavidin Alexa Fluor 350 Dye, and BODIPY TR-X Succinimidyl Ester.

A mixture of a dilution series of tubulin (500 ng/lane–0.244 ng/lane), biotin-labeled concanavalin-A (500 ng/lane–0.244 ng/lane) and a constant 250 ng/lane broad range markers (including myosin, β-galactosidase, phosphorylase b, serum albumin, ovalbumin, carbonic anhydrase, trypsin inhibitor, lysozyme and aprotinin) were separated by SDS-polyacrylamide gel electrophoresis and electroblotted as described in Example 1. The membranes were then allowed to dry to minimize loss of proteins during subsequent manipulations. The membranes were then equilibrated by incubation for 10 minutes (two times) in 10 mM sodium borate buffer, pH 9.5. After equilibration, the membranes were stained for 30 minutes with 10 µM BODIPY TR-X, SE in the same buffer. After two 5–10 mL washes in 100% methanol, the membranes were rinsed with dH$_2$O and allowed to air dry. Immunodetection was performed by standard procedures except that membranes were incubated in a mixture of a secondary goat anti-mouse IgG-alkaline phosphatase antibody and streptavidin Alexa Fluor 350. To detect the presence of the alkaline phosphatase-conjugated secondary antibody on the membranes, the membranes were incubated for 30 minutes with 10 µg/mL ELF 97 phosphate in a buffer containing 1 mM MgCl$_2$ and 10 mM Tris, pH 9.5. Proteins were viewed using 300 nm UV epi-illumination. The total protein profile appeared red fluorescent while one specific target was stained green fluorescent and the biotinylated proteins were stained blue fluorescent.

25. Trichromatic Detection of Two Specific Targets Using a Goat Anti-Mouse Secondary Antibody Conjugated to Alexa Fluor 350, ELF 97 Phosphate, and BODIPY TR-X Succinimidyl Ester.

A mixture of proteins (as in Example 24) was separated by SDS-polyacrylamide gel electrophoresis and electroblotted, as described in Example 1. The membranes were then allowed to dry to minimize loss of proteins during subsequent manipulations. The membranes were then equilibrated by incubation for 10 minutes (two times) in 10 mM sodium borate buffer, pH 9.5. After equilibration, the membranes were stained for 30 minutes with 10 µM BODIPY TR-X, SE in the same buffer. After two 5–10 minute washes in 100% methanol, the membranes were rinsed with dH$_2$O and allowed to air dry. Immunodetection was performed by standard procedures, except that membranes were incubated in a mixture of a secondary goat anti-mouse IgG-Alexa Fluor 350 conjugate and streptavidin-alkaline phosphatase. To detect the presence of the alkaline phosphatase-conjugated streptavidin on the blot the membranes were incubated for 30 minutes with 10 µg/mL ELF 97 phosphate (U.S. Pat. No. 5,316,906, incorporated by reference) in a buffer containing 1 mM MgCl$_2$ and 10 mM Tris, pH 9.5. Proteins were viewed using 300 nm UV epi-illumination. The total protein profile appeared red fluorescent while one specific target was stained blue fluorescent and the biotinylated proteins were stained green fluorescent.

26. Simultaneous Two Color Detection with In-Gel Zymography and Total-Protein Staining Using BODIPY TR-X Succinimidyl Ester.

A partially purified protein sample containing an enzyme of interest, such as β-glucuronidase, was diluted and loaded onto a standard SDS-polyacrylamide gel without boiling the sample prior to application. After separation, the gel was washed in 50 mM NaHPO$_4$ buffer, pH 7.0 (0.1% Triton X-100) and incubated in the enzymatic substrate ELF 97

β-glucuronide diluted in the same buffer (without Triton X-100). Gels were then fixed overnight in methanol:acetic acid:water (5:1:1). After fixing they were washed in dH$_2$O, equilibrated in 10 mM sodium borate buffer pH 9.5, and then incubated with 10 μM BODIPY TR-X, SE in the same buffer. Proteins were viewed using 300 nm UV trans-illumination or epi-illumination. The total protein profile appeared red fluorescent while the specific target enzyme was green fluorescent.

27. Total Protein Staining Using BODIPY Succinimidyl Esters.

Membrane staining: Proteins were separated by SDS-polyacrylamide gel electrophoresis and electroblotted, as described in Example 1. The membranes were then equilibrated by incubation for 10 minutes (two times) in 10 mM sodium borate buffer, pH 9.5. After equilibration, the blots were stained for 30 minutes with 10 μM of any BODIPY succinimidyl ester in the same buffer. After two 5–10 mL washes in 100% methanol the membranes were rinsed with dH$_2$O and allowed to dry. Proteins on membranes were viewed using UV epi-illumination.

Gel staining: Proteins were separated by SDS-polyacrylamide gel electrophoresis, as described in Example 1. The gels were then fixed overnight in methanol:acetic acid:water (5:1:1). After washing with dH$_2$O (3×30 minutes), the gels were equilibrated in 10 mM sodium borate buffer, pH 9.5. Gels were stained by incubating them 10 μM any BODIPY succinimidyl ester in the same buffer. Proteins were viewed using UV trans-illumination.

28. Screening BODIPY Succinimidyl Esters.

Standard protein molecular weight markers were serially diluted two-fold to generate a concentration range of 1000 ng–0.5 ng of protein/lane. The proteins were separated by SDS-polyacrylamide gel electrophoresis and electroblotted, as described in Example 1. The membranes were then equilibrated by incubation for 10 minutes (two times) in 10 mM sodium borate buffer, pH 9.5. After equilibration, two membranes each were stained with one of the BODIPY succinimidyl ester dyes, in Table 2. The concentration of dye used was 10 μM in 10 mM sodium borate buffer, pH 9.5. Membranes were stained for 30 minutes with agitation. The membranes were then rinsed two times, 5 minutes each time, in the same buffer. All membranes were then washed 3 times, 10 minutes each time, in 100% methanol. After a final rinse in dH$_2$O, the membranes were imaged with a constant 3 second exposure on the Bio-Rad FluorS Max MultiImager or similar device. A UV epi-illumination light source and the 520 or 610 long pass filters were used. Each dye was then imaged at its optimal exposure time, carefully avoiding signal saturation. Using the Quantity One software, the trace density for a particular protein band was determined and the background subtracted. The background-subtracted trace density was plotted versus a range of protein concentration and the linear dynamic range of detection was determined. Sensitivity was established by determining the lowest amount of protein visible on the membrane. Brightness of the dyes was compared when imaged with a common exposure time.

TABLE 2

Comparable Brightness Values of 16 BODIPY Succinimidyl Esters (SEs)

| Substitute Compound # | Abs | Em | Intensity @ 3 secs of 250 ng band of protein | | | |
|---|---|---|---|---|---|---|
| | | | Oval-bumin | Bovine Serum Albumin | Carbonic Anhydrase | Soybean Trypsin Inhibitor |
| 630/650-X | 625 | 640 | 169452.2 | 40215.84 | 193469.6 | 161528.4 |
| 650/665-X | 646 | 660 | 31163.88 | 16294.89 | 30194.71 | 26319.33 |
| TR-X | 588 | 616 | 436280.4 | 141786.4 | 558595.7 | 533819.3 |
| TMR-X | 544 | 570 | 382633.5 | 140534.5 | 564315.7 | 541307.9 |
| FL Br$_2$ | 530 | 545 | 50639.4 | 30512.31 | 70927.13 | 55972.11 |
| R6G | 528 | 547 | 116884 | 54146.32 | 227844.1 | 228890.7 |
| FL C$_5$ | 504 | 511 | 36495.05 | 36574.32 | 63640.23 | 49177.72 |
| R6G-X | 529 | 547 | 219786.1 | 148676.7 | 386058.2 | 300411.8 |
| FL | 502 | 510 | 54071.31 | 65458.51 | 71486.49 | 62468.47 |
| 530/550 | 534 | 551 | 361990.8 | 226221 | 438350.6 | 180694.7 |
| 493/503 | 500 | 509 | 24401.56 | 25658.76 | 54132.56 | 23722.79 |
| 558/568 | 559 | 568 | 130769.9 | 37031.36 | 253114.8 | 254121.8 |
| 564/570 | 563 | 569 | 383091.9 | 171803.2 | 605554.4 | 563892.1 |
| 576/589 | 575 | 588 | 78230.08 | 65072.49 | 202045.3 | 101140.1 |
| 581/591 | 581 | 591 | 208951.4 | 160171.6 | 319791.2 | 144085.5 |
| FL-X | 504 | 510 | 153667.2 | 181723.1 | 282973 | 188718.2 |

TABLE 3

Linearity and Sensitivity of Detection Values of 16 BODIPY Succinimidyl Esters (SEs) and fluorescein isothiocyanate (FITC).

| Compound # | Abs | Em | Optimal Exposure* | Sensitivity (ng of protein) | | | | Linearity Determined Using CA |
|---|---|---|---|---|---|---|---|---|
| | | | | Bovine Serum Albumin | Ovalbumin | Carbonic Anhydrase | Soybean Trypsin Inhibitor | |
| 630/650-X | 625 | 640 | 4 secs | 7.8 | 3.9 | 1.9–3.9 | 1.9–3.9 | 128-fold, $R^2 = .9813$ |
| 650/665-X | 646 | 660 | 26 secs | 3.9 | 3.9 | 1.9 | 1.9 | 256-fold, $R^2 = .9288$ |
| | | | | | | | | 16-fold, $R^2 = .9789$ |
| TR-X | 588 | 616 | 4 secs | 7.8 | 3.9–7.8 | 3.9 | 3.9–7.8 | 128-fold, $R^2 = .981$ |
| TMR-X | 544 | 570 | 3 secs | 3.9–7.8 | 3.9 | 1.9–3.9 | 3.9 | 128-fold, $R^2 = .9552$ |
| FL Br$_2$ | 530 | 545 | 10 secs | 7.8 | 7.8 | 3.9–7.8 | 7.8–15.6 | 64-fold, $R^2 = .9786$ |
| R6G | 528 | 547 | 5 secs | 7.8 | 7.8–15.6 | 1.9–3.9 | 15.6 | 128-fold, $R^2 = .9369$ |
| | | | | | | | | 64-fold, $R^2 = .9615$ |
| FL C$_5$ | 504 | 511 | 10 secs | 7.8 | 7.8 | 3.9–7.8 | 7.8–15.6 | 32-fold, $R^2 = .971$ |
| R6G-X | 529 | 547 | 4 secs | 7.8–15.6 | 3.9–7.8 | 3.9 | 3.9 | 64-fold, $R^2 = .9623$ |
| FL | 502 | 510 | 15 secs | 7.8–15.6 | 7.8–15.6 | 7.8 | 7.8 | 16-fold, $R^2 = .9872$ |
| 530/550 | 534 | 551 | 4 secs | 7.8–15.6 | 15.6 | 3.9–7.8 | 7.8–15.6 | 128-fold, $R^2 = .9577$ |
| 493/503 | 500 | 509 | 17 secs | 7.8–15.6 | 15.6–31.25 | 3.9–7.8 | 31.25 | 128-fold, $R^2 = .9516$ |
| 558/568 | 559 | 568 | 3 secs | 7.8–15.6 | 7.8 | 3.9 | 3.9–7.8 | 512-fold, $R^2 = .9645$ |
| 564/570 | 563 | 569 | 2 secs | 3.9–7.8 | 1.95–3.9 | 1.95–3.9 | 7.8 | 128-fold, $R^2 = .9907$ |
| 576/589 | 575 | 588 | 4 secs | 15.6 | 7.8 | 3.9–7.8 | 7.8 | 128-fold, $R^2 = .9922$ |

TABLE 3-continued

Linearity and Sensitivity of Detection Values of 16 BODIPY Succinimidyl Esters (SEs) and fluorescein isothiocyanate (FITC).

| | | | | Sensitivity (ng of protein) | | | | |
|---|---|---|---|---|---|---|---|---|
| Compound # | Abs | Em | Optimal Exposure* | Bovine Serum Albumin | Ovalbumin | Carbonic Anhydrase | Soybean Trypsin Inhibitor | Linearity Determined Using CA |
| 581/591 | 581 | 591 | 2 secs | 7.8–15.6 | 7.8 | 3.9 | 7.8 | 255-fold, $R^2 = .9657$ |
| FL-X | 504 | 510 | 4 secs | 3.9–7.8 | 3.9–7.8 | 1.9 | 3.9 | 256-fold, $R^2 = .9722$ |
| FITC | 494 | 519 | 10–15 sec† | 15.6–31.25 | 125 | 15.6 | 31.25 | 64-fold, $R^2 = .9797$ <br> 32-fold, $R^2 = .9936$ |

*Longest exposure without saturation †estimated

As indicated in Table 3, all of the BODIPY dyes tested, which represent a wide variety of chemical substituents on the core 4-bora-3a,4a-diazaindacene difluoride (dipyrometheneboron difluoride) core structure provided either superior sensitivity or greater linearity or both over FITC for detection of all proteins tested. Furthermore, the BODIPY dyes provided a more uniform sensitivity for protein detection that was relatively independent of the protein's structure, a properly not observed with FITC, which showed considerable differences in sensitivity depending on the nature of the protein. BODIPY dyes with the additional "X" (aminohexanoyl) that absorbed maximally between 495 nm and 640 nm showed particularly high sensitivity, uniformity of staining and good linear response. Optimal photographic exposure times, which are another measure of the sensitivity and brightness of the sample were typically shorter for the BODIPY dyes than for FITC with the preferred BODIPY dyes having an exposure time of 5 seconds or less.

29. Simultaneous Dichromatic Detection of Total Protein and a Specific Target Protein on Microarrays Using BODIPY FL-X, SE and Wheat Germ Agglutinin.

PVDF membrane was precut to a 2.5 cm×7.5 cm size. Membranes were made wet by immersing them in 100% methanol followed by immersion in water for 1 minute. Membranes were then placed on 2.5 cm×7.5 cm glass slides held to the surface of the glass by surface tension. Four specific, purified proteins including α-1 acid glycoprotein, horseradish peroxidase, immunoglobulin G and soybean trypsin inhibitor were arrayed from a source plate (384 well plate) concentration of 0.0625–4 mg/mL in PBS, onto the PVDF strips using a manual slide microarrayer. The manual arrayer was fixed with 4 rows of 8 pins (32 total) with ~500 micron diameter spot size, 1,125 micron horizontal pitch and 750 micron vertical pitch (pitch=center to center spacing of spots). The proteins were spotted in replicates of 6 resulting in an array of 192 spots including 240 ng control spots. After arraying proteins, the membranes were allowed to dry. To label total proteins the arrayed membranes were equilibrated in 35 mL of 10 mM sodium borate buffer, pH 9.5, twice for 10 minutes. After equilibration, the membranes were stained for 30 minutes with 10 μM BODIPY FL-X, succinimidyl ester in the same buffer. They were then washed twice for 2 minutes in 10 mM sodium borate buffer, pH 9.5, three times for 10 minutes in 100% methanol and finally once for 10 minutes in dH$_2$O. Membranes were then allowed to air dry. All steps, not including equilibration, were performed by placing the membranes in 50 mL centrifuge tubes and placing them on a nutator. Specific glycoprotein detection was performed by first washing the membranes for 10 minutes, three times in 50 mM Tris, pH 7.5, 150 mM NaCl followed by blocking for 1 hour in the same buffer plus 0.25% MOWIOL 4–88 and 0.2% Tween 20. For detection of glycoproteins, the membranes were incubated with 1 μg/mL wheat germ agglutinin-alkaline phosphatase conjugate in a buffer containing 50 mM Tris, pH 7.5, 150 mM NaCl, 0.2% Tween-20, 0.25% MOWIOL 4–88, 0.5 mM MgCl$_2$, and 1 mM CaCl$_2$. For detection of the conjugates, the membranes were incubated in 1.25 μg/1 nL DDAO phosphate in a buffer containing 1 mM MgCl$_2$ and 10 mM Tris, pH 9.5. Proteins were viewed using 300 nm UV epi-illumination. Wheat germ agglutinin binds glycoproteins containing N-acetylglucosamine and N-acetylneuraminic acid residues. The total protein profile appeared green fluorescent while the targeted glycoproteins (α-1 acid glycoprotein and immunoglobulin G for wheat germ agglutinin) were stained red fluorescent. Arrays can also be imaged using a laser system such as the Fuji FLA-3000 imager utilizing the 633 nm excitation filter and 675 nm emission filter for the DDAO dye and a 473 nm excitation filter and 520 nm emission filter for the BODIPY FL-X dye. Other BODIPY dyes can be utilized similarly.

30. Simultaneous Dichromatic Detection of Total Protein and a Specific Target Protein on Microarrays Using BODIPY FL-X, SE and Concanavalin A.

Proteins were arrayed, as described in Example 1. To label total proteins, the arrayed membranes were equilibrated in 35 mL of 10 mM sodium borate buffer, pH 9.5, twice for 10 minutes. After equilibration, the membranes were stained for 30 minutes with 10 μM BODIPY FL-X, succinimidyl ester in the same buffer. They were washed twice for 2 minutes in 10 mM sodium borate buffer, pH 9.5, three times for 10 minutes in 100% methanol and finally once for 10 minutes in dH$_2$O. Membranes were allowed to air dry. All steps, not including equilibration, were performed by placing the membranes in 50 mL centrifuge tubes and placing them on a nutator. Specific glycoprotein detection was performed by first washing the membranes for 10 minutes, three times in 50 mM Tris, pH 7.5, 150 mM NaCl followed by blocking for 1 hour in the same buffer plus 0.25% MOWIOL 4–88 and 0.2% Tween 20. For detection of glycoproteins, the membranes were incubated with 1 μg/nL concanavalin A-alkaline phosphatase conjugate in a buffer containing 50 mM Tris, pH 7.5, 150 mM NaCl, 0.2% Tween-20, 0.25% MOWIOL 4–88, 0.5 mM MgCl$_2$, and 1 mM CaCl$_2$. For detection of the conjugates, the membranes were incubated with 1.25 μg/mL DDAO phosphate in a buffer containing 1 mM MgCl$_2$ and 10 mM Tris, pH 9.5. Proteins were viewed using 300 nm UV epi-illumination. Concanavalin A binds to glycoproteins containing α-mannosyl and α-glucopyranosyl residues. The total protein profile appeared green fluorescent while the targeted glycoproteins (horseradish peroxidase and immunoglobulin G for concanavalin A) were stained red fluorescent. Arrays can also be imaged using a laser system such as the Fuji FLA-3000 imager utilizing the 633 nm excitation filter and 675 nm emission filter for the DDAO dye and a 473 nm excitation filter and 520 nm emission filter for the BODIPY FL-X dye. Other BODIPY dyes can be utilized similarly.

31. Simultaneous Dichromatic Detection of Total Protein and a Specific Target Protein on Microarrays with BODIPY TR-X, SE and Wheat Germ Agglutinin.

Proteins were arrayed as described in Example 1. To label total proteins the arrayed membranes were equilibrated in 35 mL of 10 mM sodium borate buffer, pH 9.5, twice for 10 minutes. After equilibration, the membranes were stained for 30 minutes in 10 μM BODIPY TR-X, succinimidyl ester in the same buffer. They were then washed twice for 2 minutes in 10 mM sodium borate buffer, pH 9.5, three times for 10 minutes in 100% methanol and finally once for 10 minutes in dH$_2$O. Membranes were allowed to air dry. All steps, not including equilibration, were performed by placing the membranes in 50 mL centrifuge tubes and placing them on a nutator. Specific glycoprotein detection was performed by first washing the membranes for 10 minutes, three times in 50 mM Tris, pH 7.5, 150 mM NaCl followed by blocking for 1 hour in the same buffer plus 0.25% MOWIOL 4–88 and 0.2% Tween 20. For detection of glycoproteins, the membranes were incubated with 1 μg/mL wheat germ agglutinin-horseradish peroxidase conjugate in a buffer containing 50 mM Tris, pH 7.5, 150 mM NaCl, 0.2% Tween-20, 0.25% MOWIOL 4–88, 0.5 mM MgCl$_2$, and 1 mM CaCl$_2$. For detection of the conjugates, the membranes were incubated with 50 μM Amplex Gold in a buffer containing 10 mM Tris, pH 7.5, 1 mM MgCl$_2$, 1 mM ZnCl$_2$ and 200 μM H$_2$O$_2$. Proteins were viewed using 300 nm UV epi-illumination. Wheat germ agglutinin binds glycoproteins containing N-acetylglucosamine and N-acetylneuraminic acid residues. The total protein profile appeared red fluorescent while the targeted glycoproteins (α-1 acid glycoprotein and immunoglobulin G for wheat germ agglutinin) were stained gold fluorescent. Arrays can also be imaged using a laser system such as the Fuji FLA-3000 imager utilizing the 633 nm excitation filter and 675 nm emission filter for the BODIPY TR-X, SE and a 532 nm excitation filter and 580 nm emission filter for the Amplex Gold. Other BODIPY dyes can be utilized similarly.

32. Simultaneous Dichromatic Detection of Total Protein and a Specific Target Protein on Microarrays with BODIPY TR-X, SE and Concanavalin A.

Proteins were arrayed, as described in Example 1. To label total proteins, the arrayed membranes were equilibrated in 35 mL of 10 mM sodium borate buffer, pH 9.5, twice for 10 minutes. After equilibration, the membranes were stained for 30 minutes with 10 μM BODIPY TR-X, succinimidyl ester in the same buffer. The membranes were washed twice for 2 minutes in 10 mM sodium borate buffer, pH 9.5, three times for 10 minutes in 100% methanol and finally once for 10 minutes in dH$_2$O. Membranes were allowed to air dry. All steps, not including equilibration, were performed by placing the membranes in 50 mL centrifuge tubes and placing them on a nutator. Specific glycoprotein detection was performed by first washing the membranes for 10 minutes, three times in 50 mM Tris, pH 7.5, 150 mM NaCl followed by blocking for 1 hour in the same buffer plus 0.25% MOWIOL 4–88 and 0.2% Tween 20. For detection of glycoproteins, the membranes were incubated with 1 μg/mL concanavalin A-alkaline phosphatase conjugate in a buffer containing 50 mM Tris, pH 7.5, 150 mM NaCl, 0.2% Tween-20, 0.25% MOWIOL 4–88, 0.5 mM MgCl$_2$, and 1 mM CaCl$_2$. For detection of the conjugates, the membranes were incubated with 10 μg/mL ELF 39 phosphate in a buffer containing 1 mM MgCl$_2$ and 10 mM Tris, pH 9.5. Proteins were viewed using 300 nm UV epi-illumination. Concanavalin A binds to glycoproteins containing α-mannosyl and α-glucopyranosyl residues. The total protein profile appeared red fluorescent while the targeted glycoproteins (horseradish peroxidase and immunoglobulin G for concanavalin A) were stained green fluorescent. Other BODIPY dyes can be utilized similarly.

What is claimed is:

1. A method of labeling poly(amino acids) comprising the steps of:
   a. separating poly(amino acids) by gel electrophoresis, resulting in separated poly (amino acids);
   b. transferring said separated poly(amino acids) to a solid support, resulting in immobilized poly(amino acids);
   c. combining said immobilized poly(amino acids) on said solid support with a labeling mixture that comprises one or more chemically reactive dipyrromethenboron difluoride dyes of the formula:

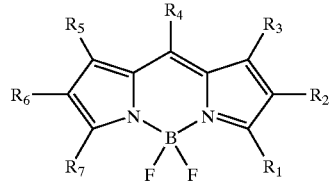

wherein each of $R^1$ through $R^7$ are independently selected from the group consisting of H, halogen, —L—Rx, substituted or unsubstituted $C_1$–$C_6$ alkyl, substituted or unsubstituted aryl, substituted or unsubstituted arylethenyl, substituted or unsubstituted arylbutadienyl, and substituted or unsubstituted heteroaryl wherein at least one of $R^1$ through $R^7$ is —L—Rx, wherein L is a spacer having 1–24 non-hydrogen atoms and Rx is a maleimide or a succinimidyl ester of a carboxylic acid;
   d. incubating the immobilized poly(amino acids) in the labeling mixture for a sufficient time for the chemically reactive dipyrromethenboron difluoride dyes to form a covalent bond with said poly(amino acids), resulting in labeled poly(amino acids).

2. A method, as claimed in claim 1, wherein Rx is a succinimidyl ester of a carboxylic acid.

3. A method, as claimed in claim 1, wherein said solid support is made of solvent-resistant materials that are selected from the group consisting of nylon, poly(vinylidene difluoride), glass, plastics, and their derivatives.

4. A method, as claimed in claim 3, wherein said solid support is poly(vinylidene difluoride).

5. A method, as claimed in claim 1, wherein said dye is present in the labeling mixture at a concentration of about 5 micromolar to about 20 micromolar.

6. A method, as claimed in claim 1, further comprising adding a specific binding pair member that contains a label and that binds selectively to a target within the immobilized poly(amino acids) that is its complementary binding pair.

7. A method of labeling poly(amino acids) bound to aptamers comprising the steps of:
   a. incubating immobilized aptamers with poly(amino acids) for a sufficient time to allow said poly(amino acids) to bind to their specific aptamers, resulting in immobilized poly(amino acids);
   b. removing unbound poly(amino acids) that are not immobilized,
   c. combining said immobilized poly(amino acids) with a labeling mixture that comprises one or more chemically reactive dipyrromethenboron difluoride dyes of the formula:

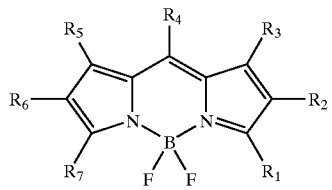

wherein each of $R^1$ through $R^7$ are independently selected from the group consisting of H, halogen, —L—Rx, substituted or unsubstituted $C_1$–$C_6$ alkyl, substituted or unsubstituted aryl, substituted or unsubstituted arylethenyl, substituted or unsubstituted arylbutadienyl, and substituted or unsubstituted heteroaryl;

provided that at least one of $R^1$ through $R^7$ is —L—Rx, wherein L is a spacer having 1–24 nonhydrogen atoms and Rx is a maleimide or a succinimidyl ester of a carboxylic acid;

d. incubating the immobilized poly(amino acids) with the labeling mixture for a sufficient time to form a covalent bond between the chemically reactive dipyrrometheneboron difluoride dye and said immobilized poly(amino acids), resulting in labeled poly(amino acids) that are bound to the aptamers.

8. A method, as claimed in claim 7, wherein Rx is a succinimidyl ester of a carboxylic acid.

9. A method, as claimed in claim 7, wherein said dipyrrometheneboron difluoride dye is present in the labeling mixture at a concentration of about 5 micromolar to about 20 micromolar.

10. A method, as claimed in claim 7, further comprising adding a specific binding pair member that contains a label and that binds selectively to a target within the immobilized poly(amino acids) that is its complementary binding pair.

11. A method of labeling immobilized poly(amino acids) in an array comprising the steps of:

a. combining an array of immobilized poly(amino acids) with a labeling mixture that comprises one or more chemically reactive dipyrrometheneboron difluoride dyes of the formula

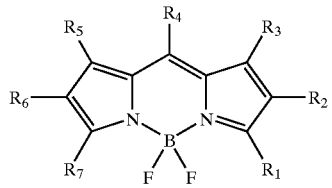

wherein each of $R^1$ through $R^7$ are independently selected from the group consisting of H, halogen, —L—Rx, substituted or unsubstituted $C_1$–$C_6$ alkyl, substituted or unsubstituted aryl, substituted or unsubstituted arylethenyl, substituted or unsubstituted arylbutadienyl, and substituted or unsubstituted heteroaryl;

provided that at least one of $R^1$ through $R^7$ is —L—Rx, wherein L is a spacer having 1–24 nonhydrogen atoms and Rx is a maleimide or a succinimidyl ester of a carboxylic acid;

b. incubating said array with the labeling mixture for a sufficient time to form a covalent bond between the dipyrrometheneboron difluoride dye and said immobilized poly(amino acids), resulting in the array of poly(amino acids) being labeled.

12. A method, as claimed in claim 11, wherein Rx said amino is a succinimidyl ester of a carboxylic acid.

13. A method, as claimed in claim 11, wherein said dipyrrometheneboron difluoride dye is present in the labeling mixture at a concentration of about 5 micromolar to about 20 micromolar.

14. A method, as claimed in claim 11, further comprising adding specific binding pair member that contains a label and that binds selectively to a target within the immobilized poly(amino acids) that is its complementary binding pair.

15. A method of detecting poly(amino acids) comprising the steps of:

a. combining poly(amino acids) immobilized on a solid support; with a labeling mixture that comprises one or more chemically reactive dipyrrometheneboron difluoride dyes of the formula

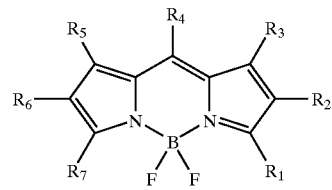

wherein each of $R^1$ through $R^7$ are independently selected from the group consisting of H, halogen, substituted or unsubstituted $C_1$–$C_6$ alkyl, substituted or unsubstituted aryl, substituted or unsubstituted arylethenyl, substituted or unsubstituted arylbutadienyl, and substituted or unsubstituted heteroaryl;

provided that at least one of $R^1$ through $R^7$ is —L—Rx, wherein L is a spacer having 1–24 nonhydrogen atoms and Rx is a maleimide or a succinimidyl ester of a carboxylic acid b. incubating said immobilized poly(amino acids) with the labeling mixture for a sufficient time to form a covalent bond between the chemically reactive dipyrrometheneboron difluoride dye and said immobilized poly(amino acids) resulting in labeled poly(amino acids);

c. removing unbound dipyrrometheneboron difluoride dyes;

d. illuminating said labeled poly(amino acids) to yield a fluorescent optical response to detect the corresponding labeled poly(amino acids).

16. A method, as claimed in claim 15, wherein the dipyrrometheneboron difluoride dye has the formula:

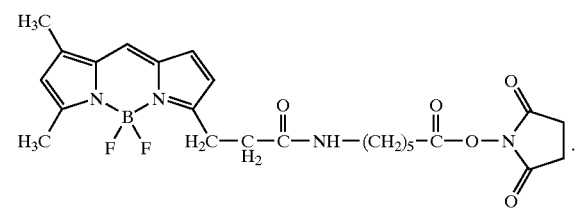

17. A method, as claimed in claim 15, wherein the dipyrromethenoboron difluoride dye has the formula:

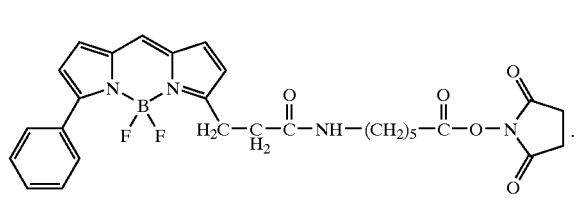

18. A method, as claimed in claim 15, wherein the dipyrromethenoboron difluoride dye has the formula:

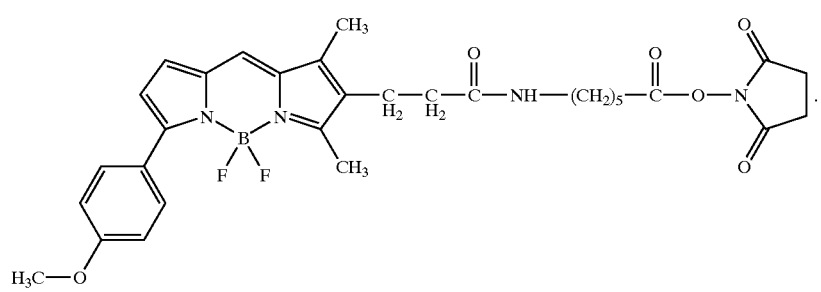

19. A method, as claimed in claim 15, wherein the dipyrromethenoboron difluoride dye has the formula:

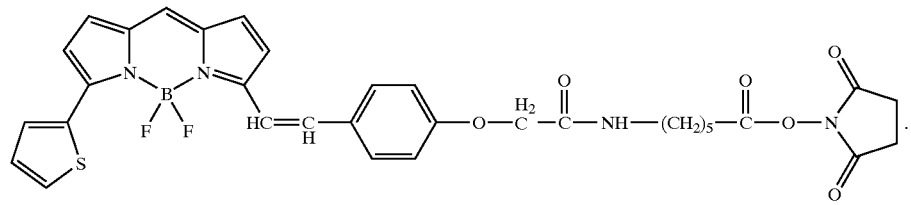

20. A method, as claimed in claim 15, wherein the dipyrromethenoboron difluoride dye has the formula:

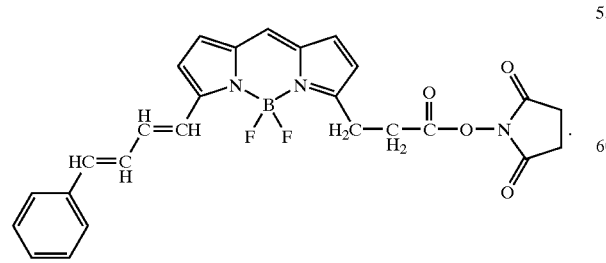

21. A method, as claimed in claim 15, wherein the dipyrromethenoboron difluoride dye has the formula:

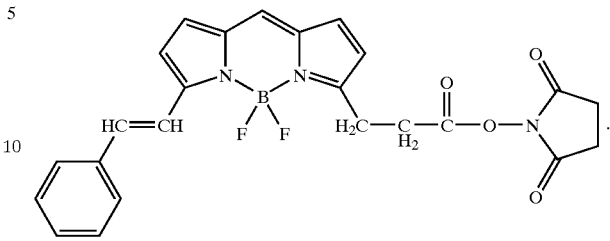

22. A method, as claimed in claim 15, wherein the dipyrromethenoboron difluoride dye has the formula:

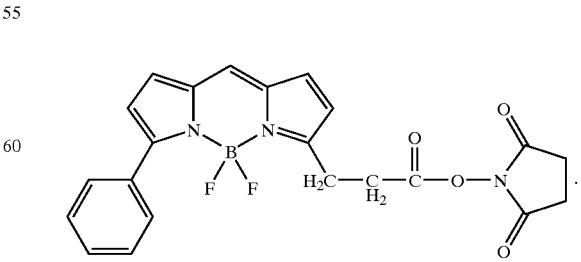

23. A method, as claimed in claim 15, wherein the dipyrromethene boron difluoride dye has the formula:

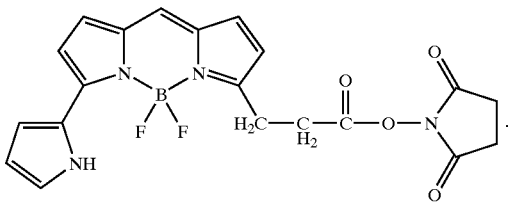

24. A method, as claimed in claim 15, wherein the dipyrromethene boron difluoride dye has the formula:

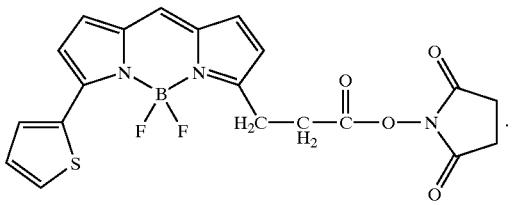

25. A method, as claimed in claim 15, wherein the dipyrromethene boron difluoride dye has the formula:

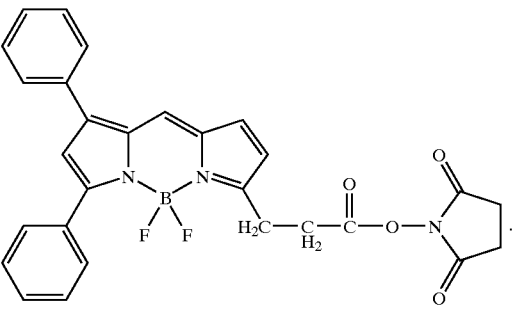

26. A method, as claimed in claim 15, wherein the dipyrromethene boron difluoride dye has the formula:

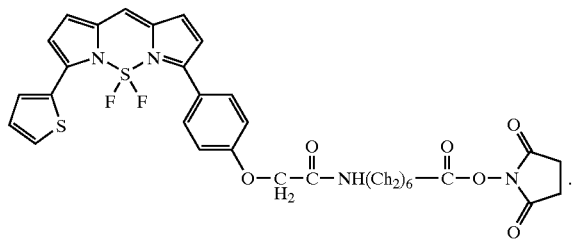

27. A method, as claimed in claim 15, wherein said solid support is made of solvent-resistant materials that are selected from the group consisting of nylon, poly(vinylidene difluoride), glass, plastics, and their derivatives.

28. A method, as claimed in claim 27, wherein said solid support is poly(vinylidene difluoride).

29. A method, as claimed in claim 15, wherein said dipyrromethene boron difluoride dye is present in the labeling mixture at a concentration of about 5 micromolar to about 20 micromolar.

30. A method, as claimed in claim 15, further comprising adding a specific binding pair member that selectively binds to a target within said immobilized poly(amino acids) that is its complementary binding pair.

31. A method, as claimed in claim 30, where said specific binding pair member contains a label that is an enzyme or a hapten.

32. A method, as claimed in claim 30, where said specific binding pair member contains a label that is a fluorophore.

33. A method, as claimed in claim 30, further comprising:
adding a secondary complementary binding pair member that contains a label and that selectively binds to the specific binding pair member.

34. A method, as claimed in claim 33, wherein the label on the secondary complementary binding pair is an enzyme.

35. A method, as claimed in claim 33, wherein the label on the secondary complementary binding pair is a fluorescent dye.

36. A method, as claimed in claim 34, wherein said enzyme is a peroxidase or a phosphatase.

37. A method, as claimed in claim 36, wherein said peroxidase is horseradish peroxidase.

38. A method, as claimed in claim 36 wherein said phosphatase is alkaline phosphatase.

39. A method, as claimed in claim 34, wherein said enzyme is capable of utilizing a fluorogenic substrate to generate a detectable optical response.

40. A method, as claimed in claim 39, wherein said enzyme is a peroxidase and said fluorogenic substrate is a fluorescent tyramide.

41. A method, as claimed in claim 39, wherein said enzyme is a phosphatase and said fluorogenic substrate is a quinazolinone phosphate.

42. A method, as claimed in claim 39, wherein said enzyme is a phosphatase and said fluorogenic substrate is 9H-(1,3-dichloro-9,9-dimethylacridin-2-one-7-yl) phosphate.

43. A method, as claimed in claim 39, wherein said enzyme is a peroxidase and said fluorogenic substrate is a polyfluorinated xanthene.

44. A method, as claimed in claim 33, wherein said secondary complimentary binding pair is an antibody or an antibody fragment.

45. A method, as claimed in claim 32, wherein said complementary specific binding pair member is a lectin.

46. A method, as claimed in claim 32, wherein said specific binding pair member is biotin-binding protein that contains a label.

47. A method, as claimed in claim 46, wherein said biotin-binding protein is streptavidin.

48. A method, as claimed in claim 46, wherein said biotin-binding protein is NeutrAvidin.

49. A method, as claimed in claim 30, wherein said specific binding pair member is an antibody or antibody fragment, an aptamer, a lectin, or a biotin-binding protein.

50. A method, as claimed in claim 1, wherein said dye is selected from the group consisting of
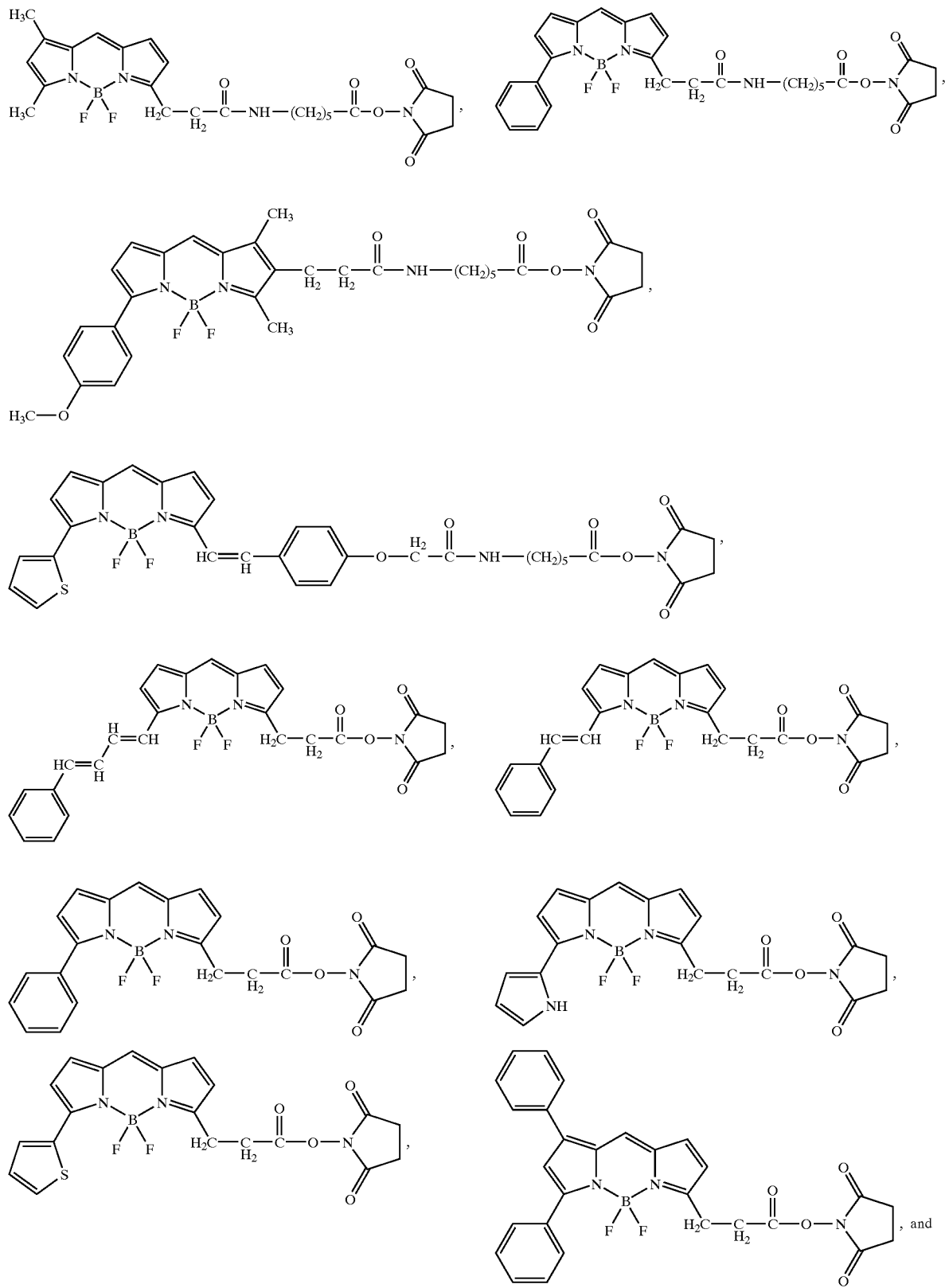

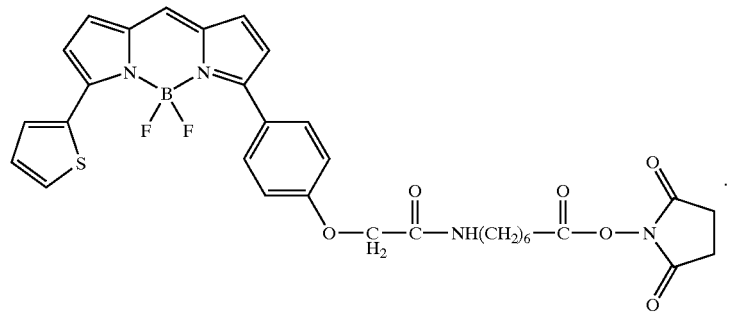
51. A method, as claimed in claim 7, wherein said dye is selected from the group consisting of
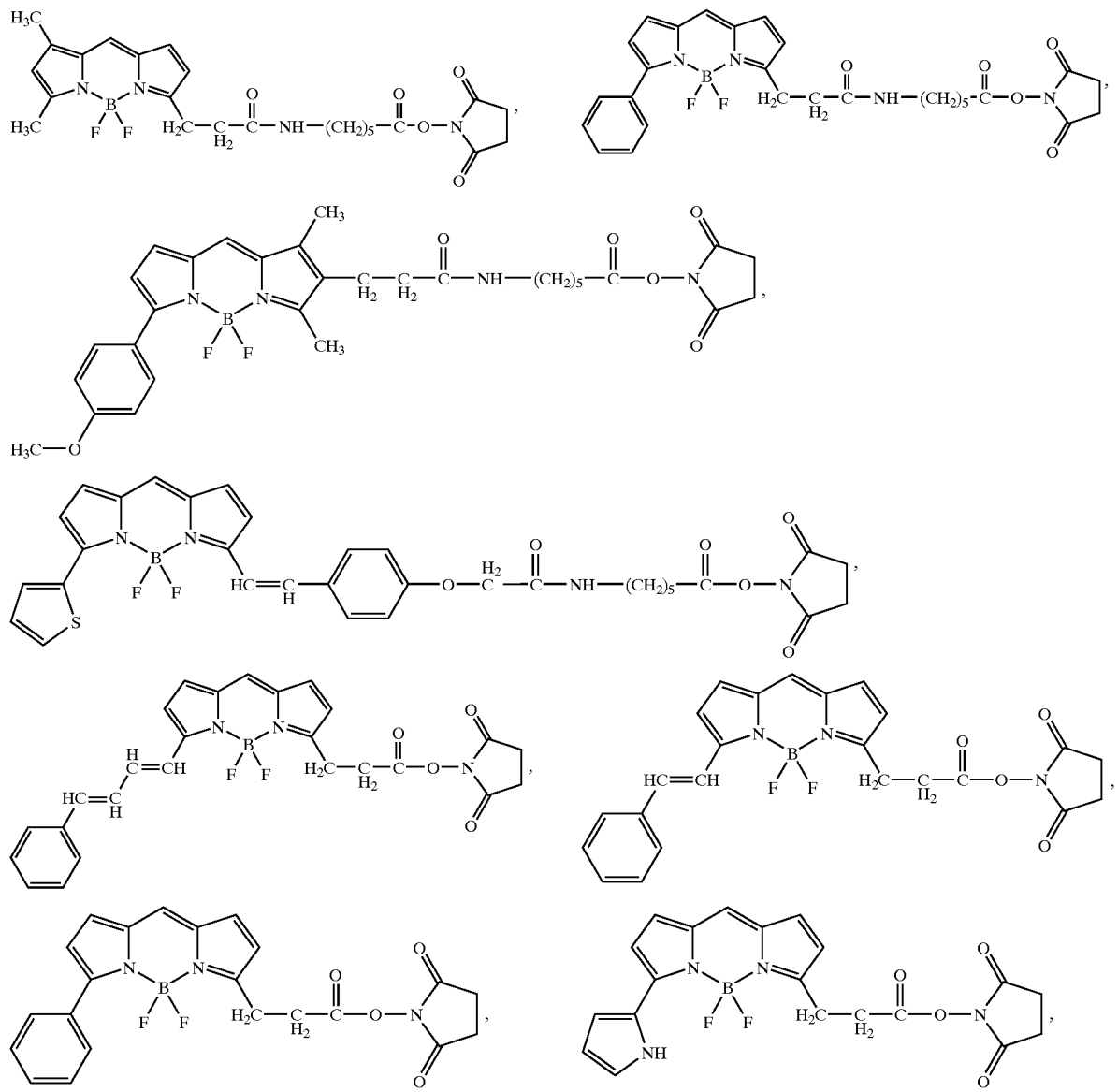

-continued

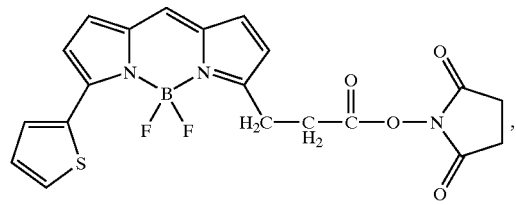

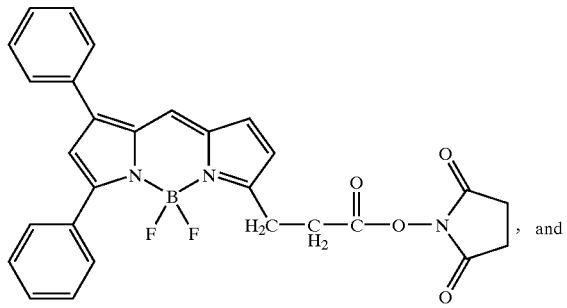

and

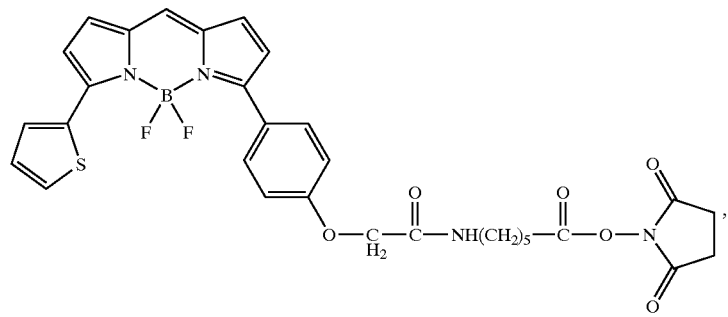

52. A method of detecting immobilized poly(amino acids) comprising the steps of:
a) separating poly(amino acids) by gel electrophoresis, resulting in separated poly (amino acids);
b) transferring said separated poly(amino acids) to a solid support, resulting in immobilized poly(amino acids);
c) combining said immobilized poly(amino acids) on said solid support with a labeling mixture that comprises one or more chemically reactive dipyrrometheneboron difluoride dyes of the formula:

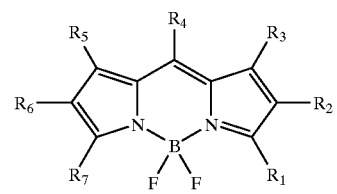

wherein each of $R^1$ through $R^7$ are independently selected from the group consisting of H, halogen, —L—Rx, substituted or unsubstituted $C_1$–$C_6$ alkyl substituted or unsubstituted aryl, substituted or unsubstituted arylethenyl, substituted or unsubstituted arylbutadienyl, and substituted or unsubstituted heteroaryl;
wherein at least one of $R^1$ through $R^7$ is —L—Rx, wherein L is a spacer having 1–24 nonhydrogen atoms and Rx is a maleimide or a succinimidyl ester of a carboxylic acid;

d) incubating the immobilized poly(amino acids) in the labeling mixture for a sufficient time for the chemically reactive dipyrrometheneboron difluoride dyes to form a covalent bond with said poly(amino acids), resulting in labeled poly(amino acids);
e) removing unbound dipyrrometheneboron difluoride dyes;
f) illuminating said labeled poly(amino acids) to yield a fluorescent optical response to detect the corresponding labeled poly(amino acids).

53. A method, as claimed in claim 52, wherein said solid support is made of solvent-resistant materials that are selected from the group consisting of nylon, poly(vinylidene difluoride), glass, plastics, and their derivatives.

54. A method, as claimed in claim 52, wherein said solid support is poly(vinylidene difluoride).

55. A method, as claimed in claim 52, wherein said dipyrrometheneboron difluoride dye is present in the labeling mixture at a concentration of about 5 micromolar to about 20 micromolar.

56. A method, as claimed in claim 52, further comprising adding a specific binding pair member that selectively binds to a target within said immobilized poly(amino acids) that is its complementary binding pair.

57. A method, as claimed in claim 56, where said specific binding pair member contains a label that is an enzyme, a fluorophore or a hapten.

58. A method, as claimed in claim 56, further comprising:
adding a secondary complementary binding pair member that contains a label and that selectively binds to the specific binding pair member.

59. A method, as claimed in claim 52, wherein said dye is selected from the group consisting of
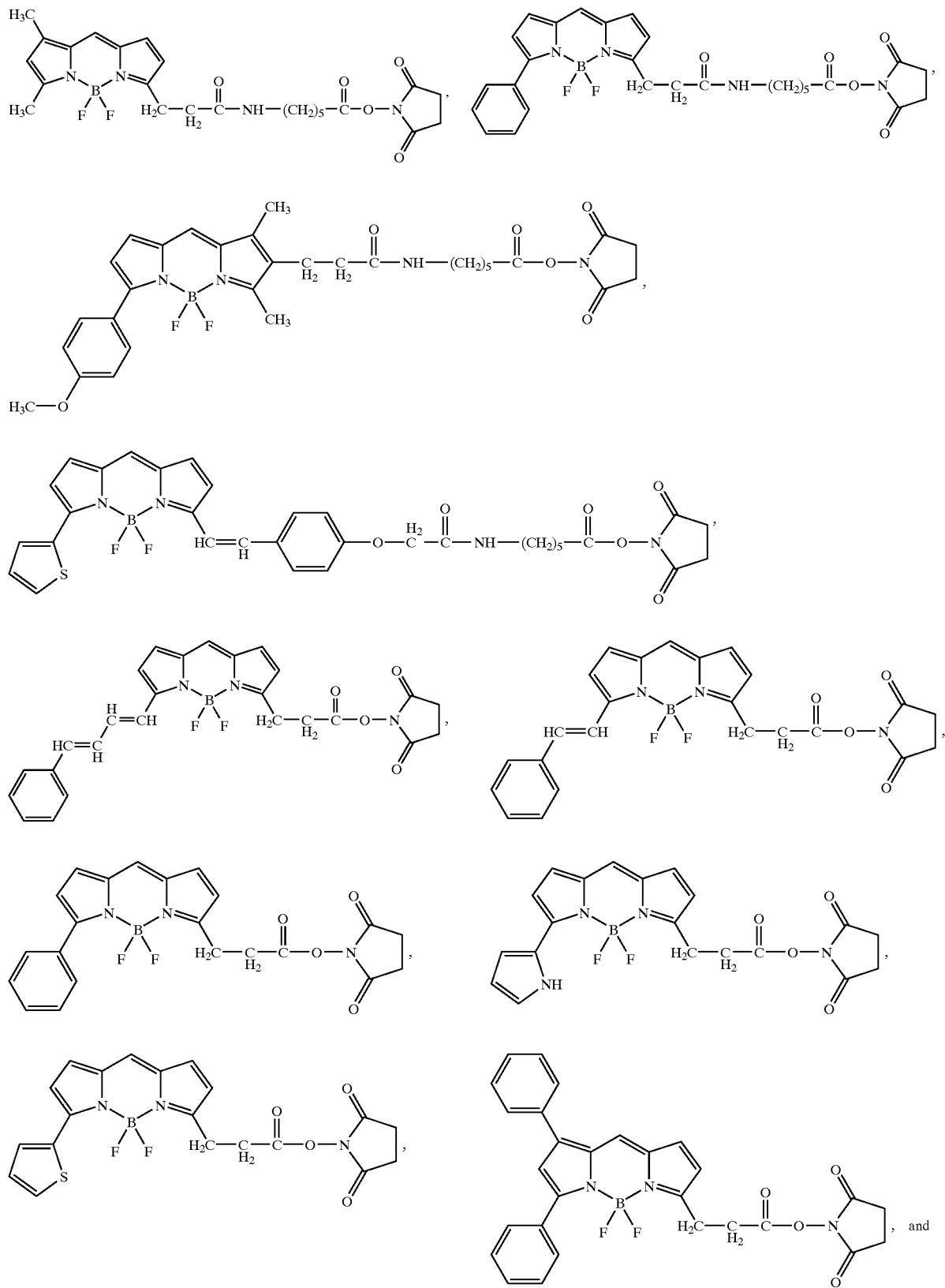

-continued
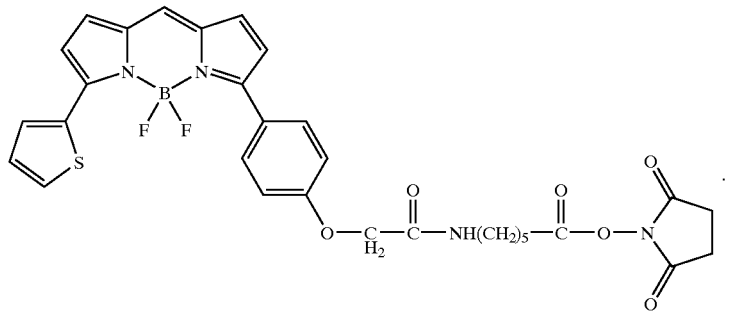
* * * * *